(12) United States Patent
Shelton, IV et al.

(10) Patent No.: US 10,779,828 B2
(45) Date of Patent: Sep. 22, 2020

(54) SURGICAL INSTRUMENT WITH CAPACITIVE ELECTRICAL INTERFACE

(71) Applicant: ETHICON LLC, Guaynabo, PR (US)

(72) Inventors: Frederick E. Shelton, IV, Hillsboro, OH (US); David C. Yates, West Chester, OH (US); Jason L. Harris, Lebanon, OH (US); Jerome R. Morgan, Cincinnati, OH (US); Gregory J. Bakos, Mason, OH (US); Nichole Y. Kwee, Cincinnati, OH (US); John E. Brady, Liberty Township, OH (US)

(73) Assignee: Ethicon LLC, Guaynabo, PR (US)

( * ) Notice: Subject to any disclaimer, the term of this patent is extended or adjusted under 35 U.S.C. 154(b) by 255 days.

(21) Appl. No.: 15/934,180

(22) Filed: Mar. 23, 2018

(65) Prior Publication Data
US 2019/0290272 A1    Sep. 26, 2019

(51) Int. Cl.
*A61B 17/072*    (2006.01)
*A61B 17/00*    (2006.01)
(Continued)

(52) U.S. Cl.
CPC .. *A61B 17/07207* (2013.01); *A61B 17/00234* (2013.01); *A61B 17/115* (2013.01);
(Continued)

(58) Field of Classification Search
CPC .... A61B 17/07207; A61B 2017/07271; A61B 2017/00017
See application file for complete search history.

(56) References Cited

U.S. PATENT DOCUMENTS 5,535,937 A  *  7/1996  Boiarski .......... A61B 17/07207
                                                    227/175.3
5,792,135 A     8/1998  Madhani et al.
(Continued)

FOREIGN PATENT DOCUMENTS

EP    2 839 797 A2    2/2015
WO   WO 2010/090941 A1   8/2010
WO   WO 2015/153642 A1  10/2015

OTHER PUBLICATIONS

Hollister, S., "Waterproofing explained: How Apple, Samsung and Sony keep the liquid out," clnet.com, Sep. 21, 2016, downloaded from https://www.cnet.com/news/how-does-waterproofing-work-apple-iphone-7-samsung-galaxy-s7-sony-xperia/, copyrighted by CBS Interactive Inc., 8 pgs.
(Continued)

*Primary Examiner* — Andrew M Tecco
(74) *Attorney, Agent, or Firm* — Frost Brown Todd LLC

(57) ABSTRACT

A surgical instrument includes a body, a shaft assembly, an end effector, and an electrical contact assembly. The shaft assembly extends distally from the body. The end effector includes a channel assembly and a cartridge assembly configured to selectively couple with the channel assembly. The channel assembly includes an electrically activated component. The electrical contact assembly is configured to electrically couple a power source with the electrically activated component of the cartridge assembly. The electrical contact assembly includes a first conductive plate associated with the channel assembly, a second conductive plate associated with the cartridge assembly, and a dielectric cover. The dielectric cover is associated with either the first conductive plate or the second conductive plate. The dielectric cover is
(Continued)

positioned between the first conductive plate and the second conductive plate when the cartridge assembly is coupled with the channel assembly.

20 Claims, 15 Drawing Sheets

(51) Int. Cl.
  *A61B 17/115* (2006.01)
  *A61N 1/40* (2006.01)
(52) U.S. Cl.
  CPC .............. *A61B 2017/00022* (2013.01); *A61B 2017/07271* (2013.01); *A61N 1/40* (2013.01)

(56) References Cited

U.S. PATENT DOCUMENTS

| | | | |
|---|---|---|---|
| 5,817,084 A | | 10/1998 | Jensen |
| 5,817,093 A | | 10/1998 | Williamson, IV et al. |
| 5,878,193 A | | 3/1999 | Wang et al. |
| 6,231,565 B1 | | 5/2001 | Tovey et al. |
| 6,364,888 B1 | | 4/2002 | Niemeyer et al. |
| 6,783,524 B2 | | 8/2004 | Anderson et al. |
| 7,404,508 B2 | | 7/2008 | Smith et al. |
| 7,524,320 B2 | | 4/2009 | Tierney et al. |
| 7,691,098 B2 | | 4/2010 | Wallace et al. |
| 7,721,930 B2 | | 5/2010 | McKenna et al. |
| 7,806,891 B2 | | 10/2010 | Nowlin et al. |
| 7,900,805 B2 | * | 3/2011 | Shelton, IV ..... A61B 17/07207 227/175.1 |
| 8,083,120 B2 | * | 12/2011 | Shelton, IV ..... A61B 17/07207 227/180.1 |
| 8,408,439 B2 | | 4/2013 | Huang et al. |
| 8,453,914 B2 | | 6/2013 | Laurent et al. |
| 8,479,969 B2 | | 7/2013 | Shelton, IV |
| 8,573,461 B2 | | 11/2013 | Shelton, IV et al. |
| 8,573,465 B2 | | 11/2013 | Shelton, IV |
| 8,602,288 B2 | | 12/2013 | Shelton, IV et al. |
| 8,608,045 B2 | | 12/2013 | Smith et al. |
| 8,616,431 B2 | | 12/2013 | Timm et al. |
| 8,783,541 B2 | | 7/2014 | Shelton, IV et al. |
| 8,800,838 B2 | | 8/2014 | Shelton, IV |
| 8,820,605 B2 | | 9/2014 | Shelton, IV |
| 8,844,789 B2 | | 9/2014 | Shelton, IV et al. |
| 8,991,678 B2 | | 3/2015 | Wellman et al. |
| 9,072,535 B2 | | 7/2015 | Shelton, IV et al. |
| 9,186,142 B2 | | 11/2015 | Fanelli et al. |
| 9,301,759 B2 | | 4/2016 | Spivey et al. |
| 9,345,481 B2 | | 5/2016 | Hall et al. |
| 9,724,094 B2 | | 8/2017 | Baber et al. |
| 9,795,379 B2 | | 10/2017 | Leimbach et al. |
| 9,839,425 B2 | | 12/2017 | Zergiebel et al. |
| 9,913,642 B2 | | 3/2018 | Leimbach et al. |
| 2008/0164296 A1 | * | 7/2008 | Shelton ............ A61B 17/07207 227/175.1 |
| 2008/0167644 A1 | * | 7/2008 | Shelton ............ A61B 17/07207 606/34 |
| 2010/0065605 A1 | * | 3/2010 | Shelton, VI ...... A61B 17/07207 227/176.1 |
| 2011/0024478 A1 | * | 2/2011 | Shelton, IV ..... A61B 17/07207 227/176.1 |
| 2014/0263541 A1 | | 9/2014 | Leimbach et al. |
| 2014/0263552 A1 | | 9/2014 | Hall et al. |
| 2016/0066911 A1 | | 3/2016 | Baber et al. |
| 2016/0310134 A1 | | 10/2016 | Contini et al. |

OTHER PUBLICATIONS

U.S. Appl. No. 15/635,663, filed Jun. 28, 2017.
U.S. Appl. No. 15/635,631, filed Jun. 28, 2017.
U.S. Appl. No. 15/635,837, filed Jun. 28, 2017.
U.S. Appl. No. 15/636,096, filed Jun. 28, 2017.
U.S. Appl. No. 15/934,139, filed Mar. 23, 2018.
U.S. Appl. No. 15/934,148, filed Mar. 23, 2018.
U.S. Appl. No. 15/934,160, filed Mar. 23, 2018.
U.S. Appl. No. 15/934,166, filed Mar. 23, 2018.
U.S. Appl. No. 15/934,173, filed Mar. 23, 2018.
U.S. Appl. No. 15/934,190, filed Mar. 23, 2018.
European Search Report and Written Opinion dated Aug. 2, 2019 for Application No. EP 19164696.7, 7 pgs.
International Search Report and Written Opinion dated Aug. 5, 2019 for Application No. PCT/IB2019/052315, 11 pgs.

* cited by examiner

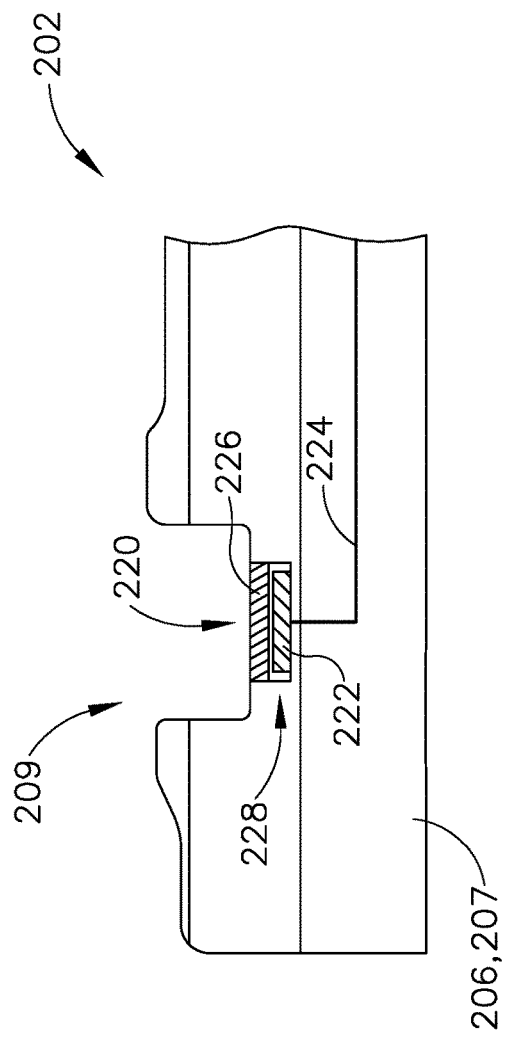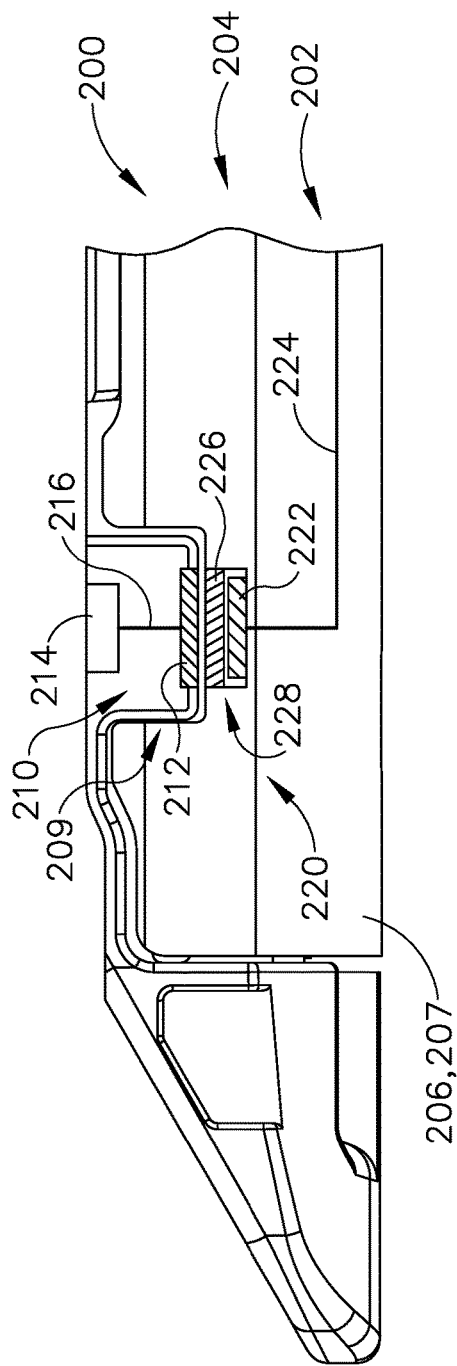

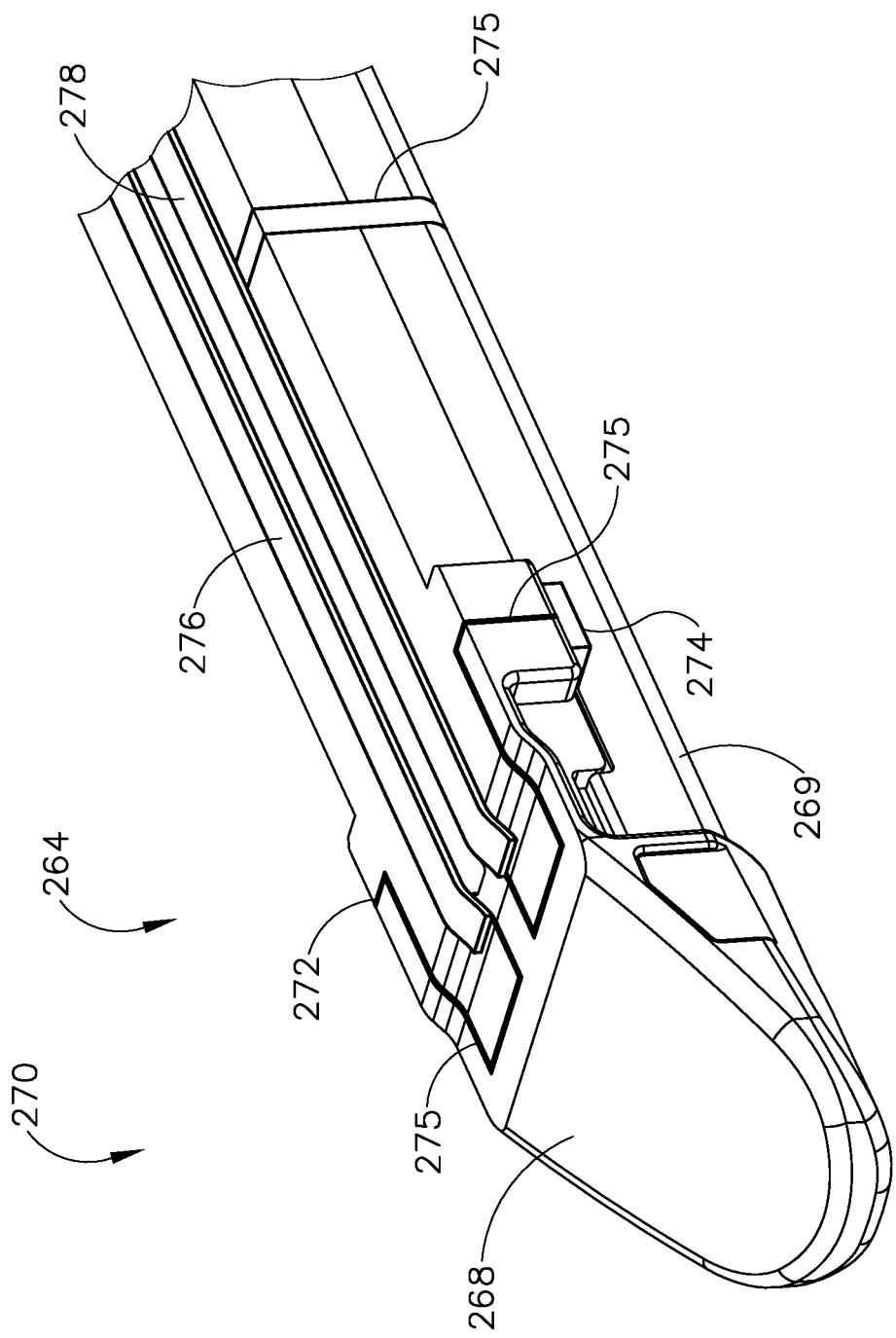

SURGICAL INSTRUMENT WITH CAPACITIVE ELECTRICAL INTERFACE

BACKGROUND

Endoscopic surgical instruments may be preferred over traditional open surgical devices in certain instances to create a smaller surgical incision in the patient and thereby reduce the post-operative recovery time and complications. Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 7,404,508, entitled "Surgical Stapling and Cutting Device," issued Jul. 29, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; U.S. Pat. No. 8,453,914, entitled "Motor-Driven Surgical Cutting Instrument with Electric Actuator Directional Control Assembly," issued Jun. 4, 2013; U.S. Pat. No. 9,186,142, entitled "Surgical Instrument End Effector Articulation Drive with Pinion and Opposing Racks," issued Nov. 17, 2015; and U.S. Pat. No. 9,795,379, entitled "Surgical Instrument with Multi-Diameter Shaft," issued Oct. 24, 2017. The disclosure of each of the above-cited U.S. patents is incorporated by reference herein.

While the surgical staplers referred to above are described as being used in endoscopic procedures, such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Of course, surgical staplers may be used in various other settings and procedures.

While several surgical instruments and systems have been made and used, it is believed that no one prior to the inventors has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 10 depicts a side cross-sectional view of a portion of the elongate channel of FIG. 9;

FIG. 11 depicts a side cross-sectional view of a portion of a staple cartridge coupled with the elongate channel of FIG. 9;

FIG. 16 depicts a perspective view of a distal portion of an exemplary cartridge that may be coupled with the elongate channel shown in FIG. 15.

Figure 1:
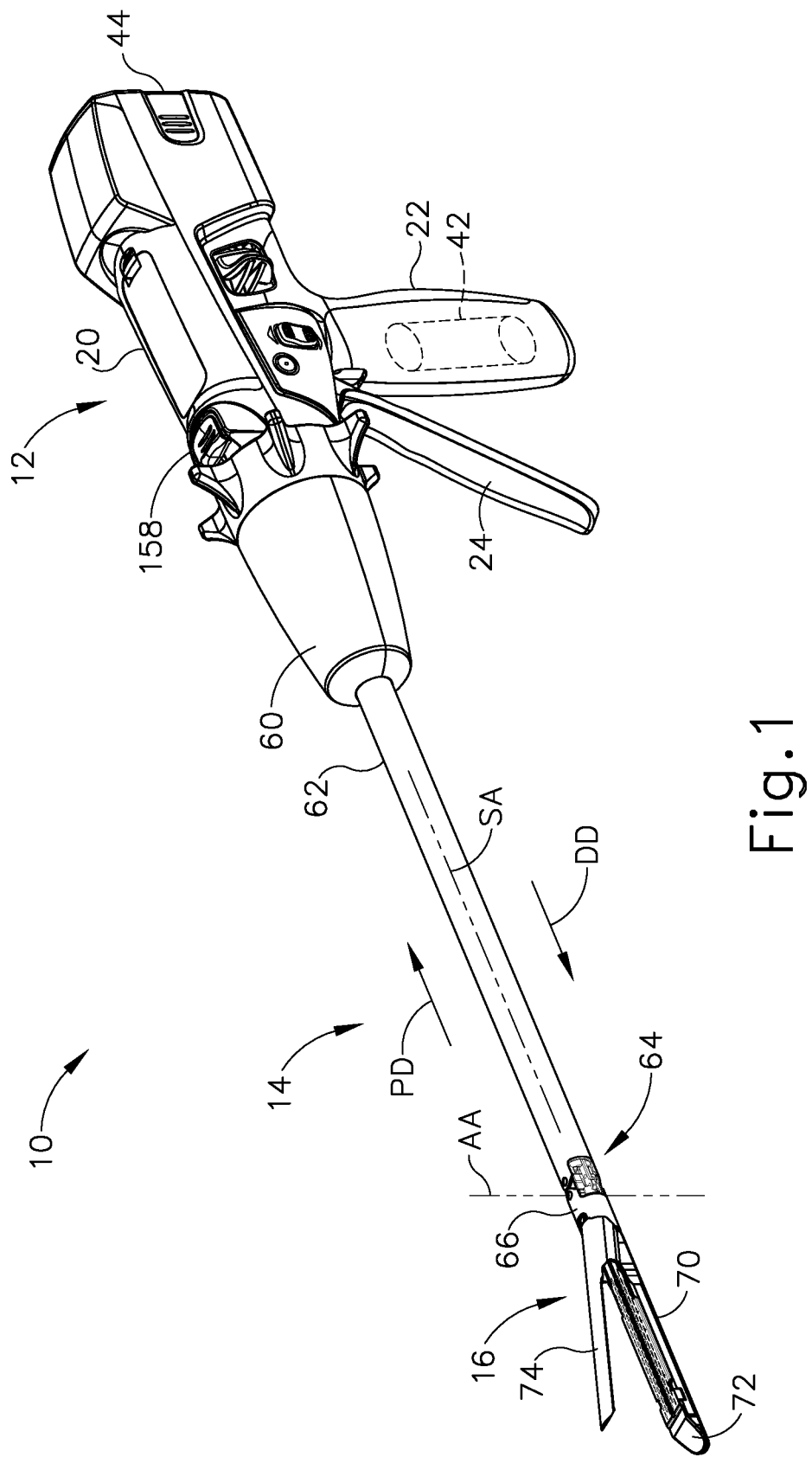
FIG. 1 depicts a perspective view of an exemplary surgical instrument having a handle assembly and an interchangeable shaft assembly.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, clinician, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

As used herein, the terms "about" and "approximately" for any numerical values or ranges indicate a suitable dimensional tolerance that allows the part or collection of components to function for its intended purpose as described herein.

I. EXEMPLARY SURGICAL STAPLING INSTRUMENT

Figure 2:
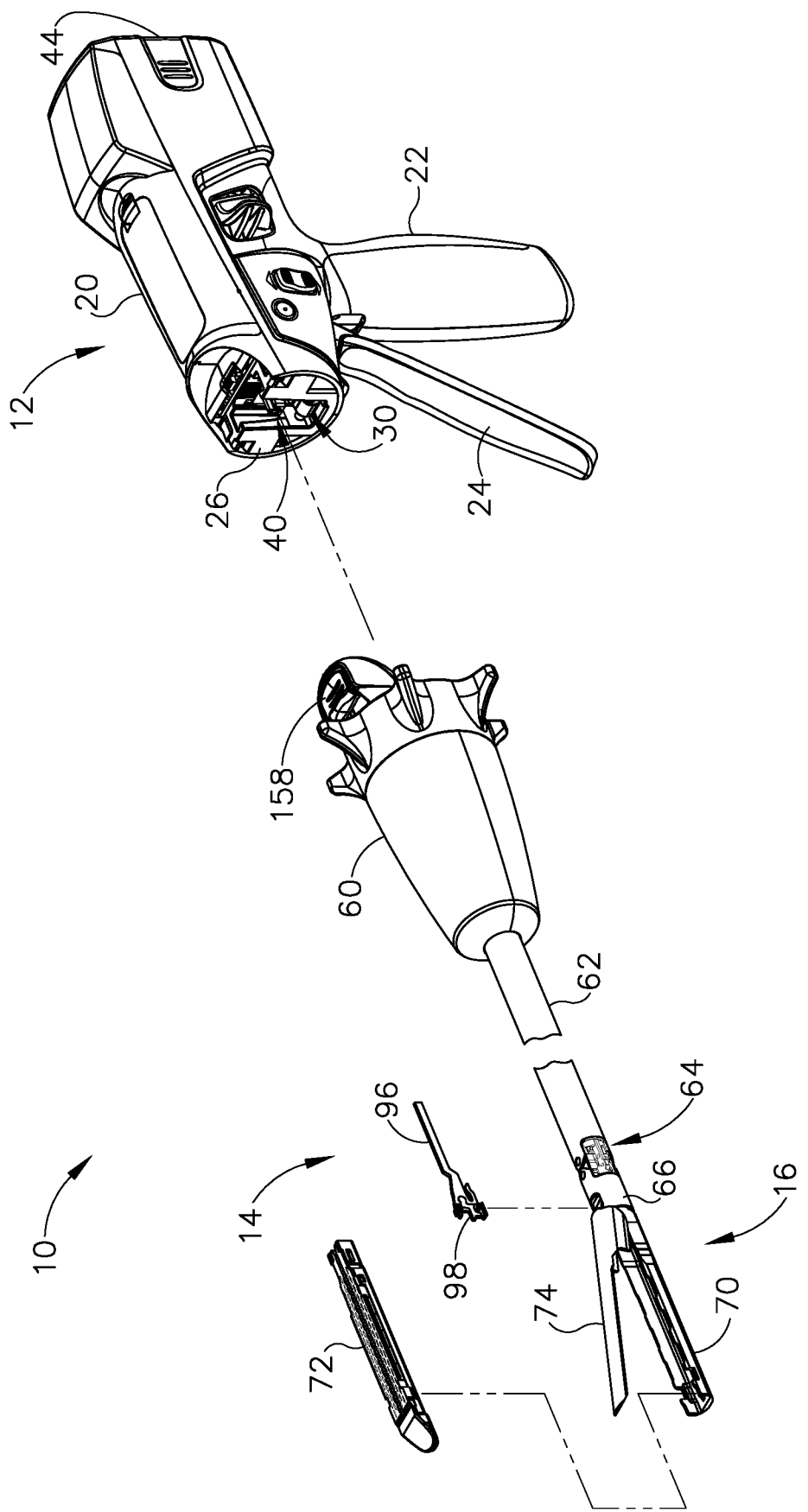
FIG. 2 depicts a partially exploded perspective view of the surgical instrument of FIG. 1, showing the interchangeable shaft assembly separated from the handle assembly.

FIGS. 1-2 show a motor-driven surgical instrument (10) suitable for use in a variety of surgical procedures. In the illustrated example, instrument (10) includes a handle assembly (12) and an interchangeable shaft assembly (14) releasably coupled to and extending distally from handle assembly (12). Interchangeable shaft assembly (14) includes a surgical end effector (16) arranged at a distal end thereof, and which is configured to perform one or more surgical tasks or procedures. In some applications, interchangeable shaft assembly (14) may be effectively employed with a tool drive assembly of a robotically controlled or automated surgical system. For example, interchangeable shaft assembly (14) may be employed with various robotic systems, instruments, components, and methods such as those disclosed in U.S. Pat. No. 9,072,535, entitled "Surgical Stapling Instruments With Rotatable Staple Deployment Arrangements," issued Jul. 7, 2015, the disclosure of which is incorporated by reference herein.

A. Handle Assembly of Surgical Stapling Instrument

Handle assembly (12) comprises a body (20) that includes a pistol grip (22) configured to be grasped by a clinician, and a closure trigger (24) configured to pivot toward and away from pistol grip (22) to selectively close and open end effector (16), as described in greater detail below. In the present example, end effector (16) is configured to cut and staple tissue captured by end effector (16). In other examples, end effector (16) may be configured to treat tissue via application of various other types of movements and energies, such as radio frequency (RF) energy and/or ultrasonic energy, for example.

Figure 3A:
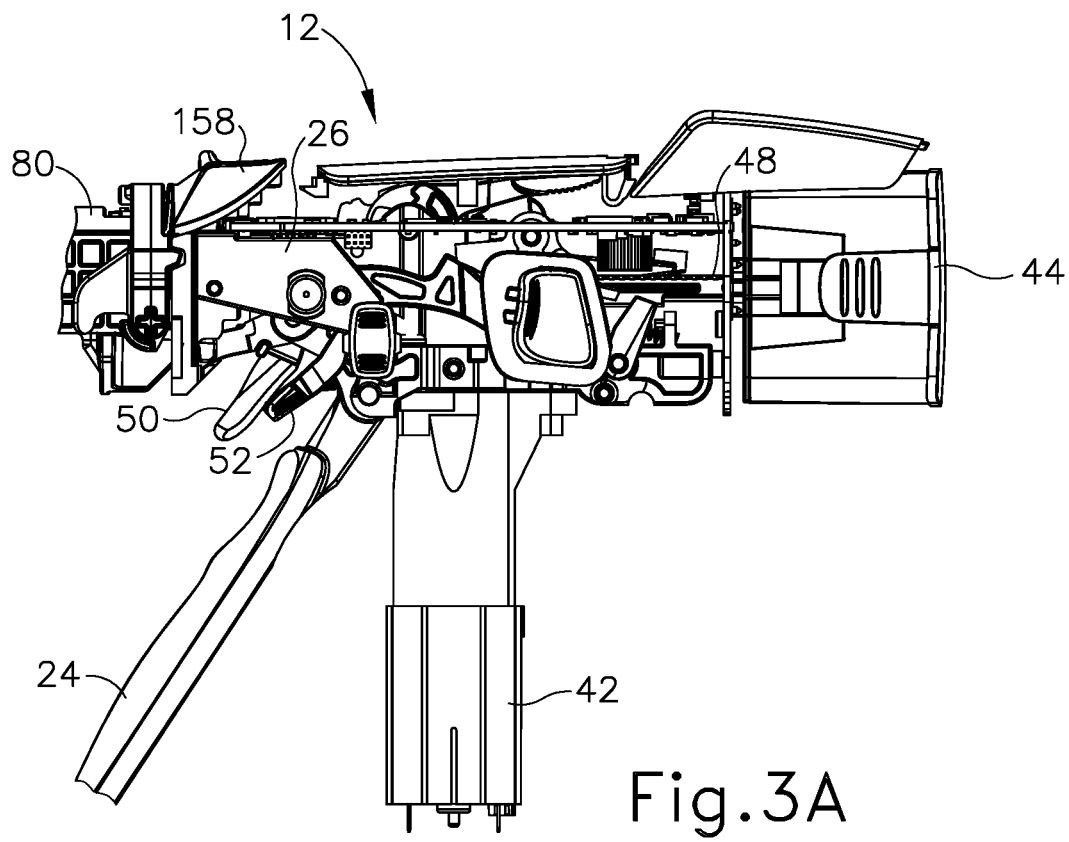
FIG. 3A depicts a side elevational view of the surgical instrument of FIG. 1, with a body of the handle assembly omitted, showing a closure trigger of the handle assembly in an unactuated position.
Figure 3B:
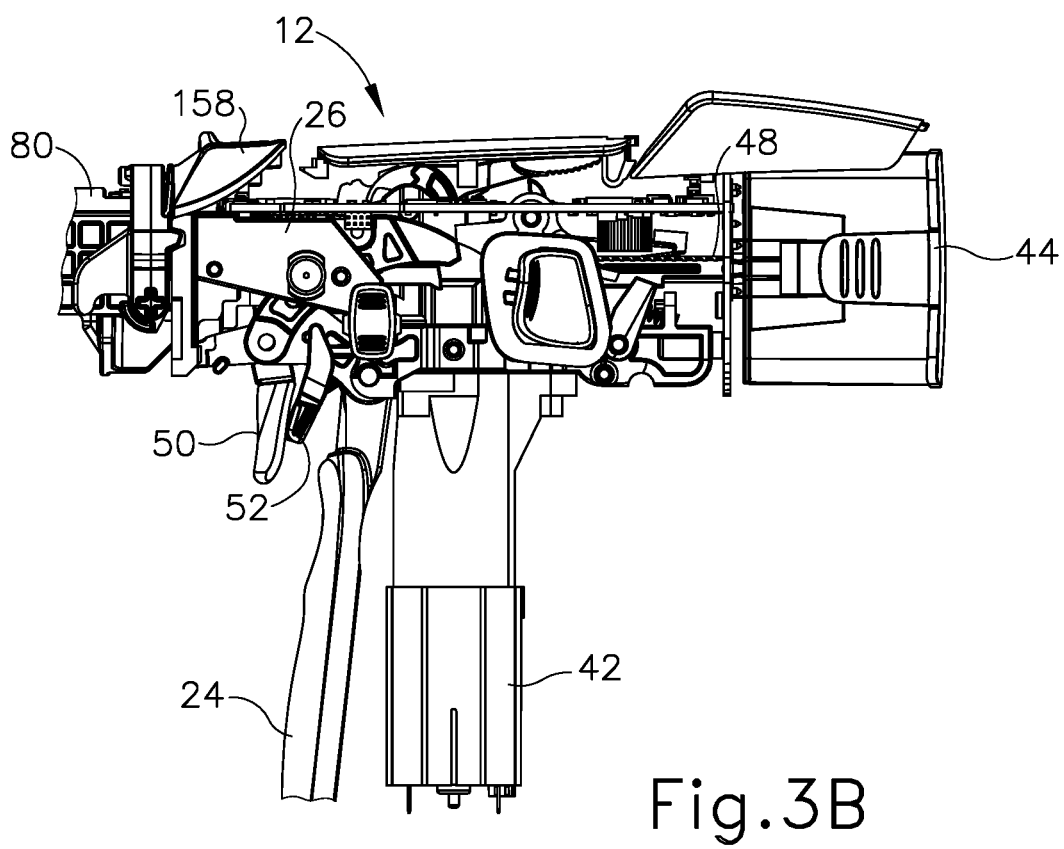
FIG. 3B depicts a side elevational view of the surgical instrument of FIG. 1, with a body of the handle assembly omitted, showing a closure trigger of the handle assembly in an actuated position.
Figure 4:
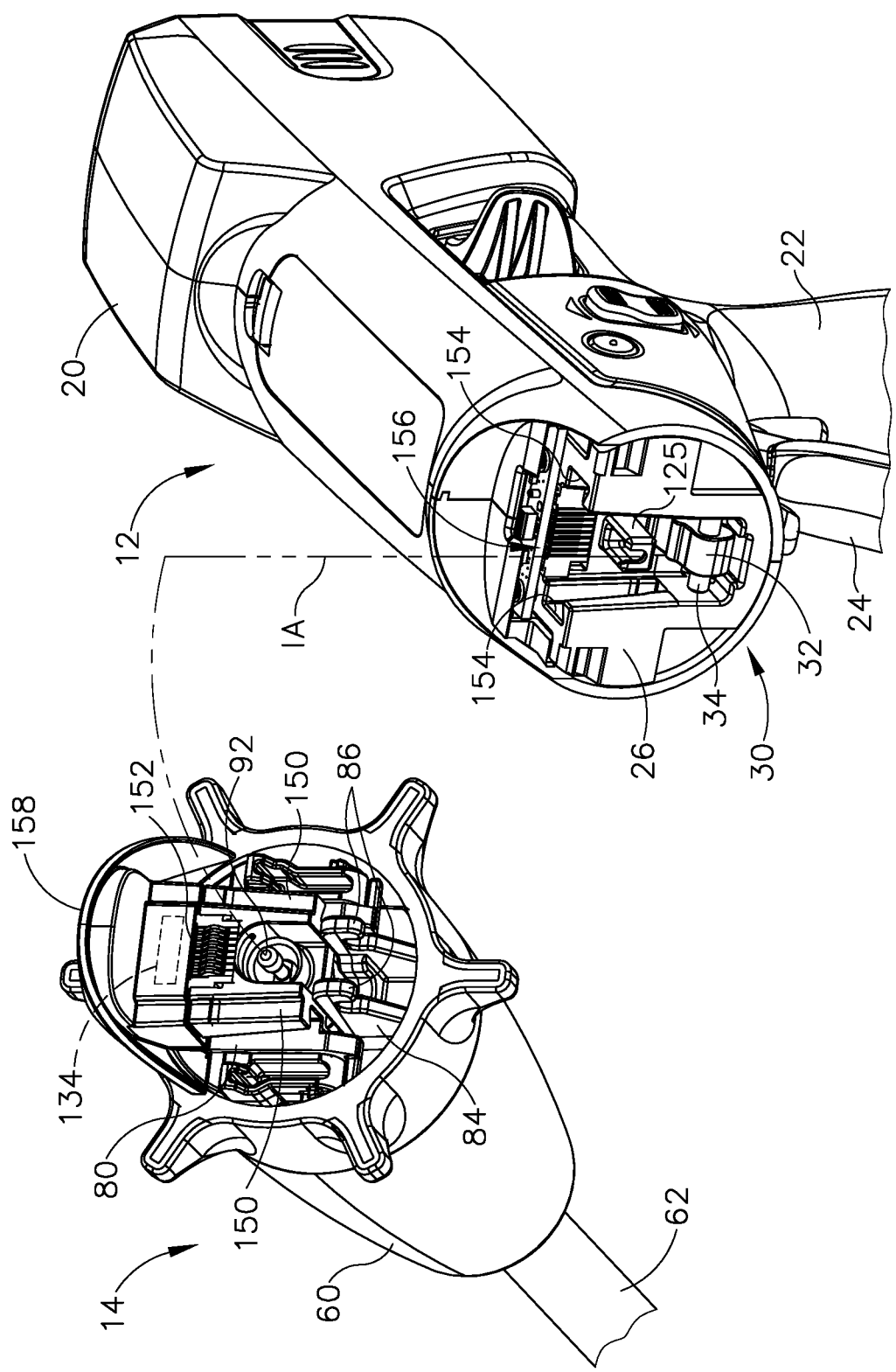
FIG. 4 depicts another perspective view of the surgical instrument of FIG. 1 in a separated state, showing additional details of a distal end of the handle assembly and a mating proximal end of the interchangeable shaft assembly.

As seen in FIGS. 2-4, handle assembly body (20) houses a handle frame (26) that supports a plurality of drive systems configured to generate and apply various control motions to corresponding portions of interchangeable shaft assembly (14). In particular, handle frame (26) supports a first drive system in the form of a closure drive system (30) that is operable to selectively close and open end effector (16) to thereby capture and release tissue. Closure drive system (30) includes an actuator in the form of closure trigger (24), which is pivotally supported by handle frame (26) and is operatively coupled with end effector (16) via components of shaft assembly (14) described below. Closure trigger (24) is configured to be squeezed by a clinician toward pistol grip (22) from an unactuated position (FIG. 3A) that provides end effector (16) in an open state for releasing tissue, to an actuated position (FIG. 3B) that provides end effector (16) in a closed state for clamping tissue. Closure trigger (24) may be biased toward the unactuated position by a resilient member (not shown). As seen best in FIG. 4, closure drive system (30) further comprises a linkage assembly that couples closure trigger (24) with end effector (16). The linkage assembly includes a closure link (32) and a transversely extending attachment pin (34) coupled to a distal end of closure link (32). Attachment pin (34) and the distal end of closure link (32) are accessible through a distal opening in handle assembly (12).

Handle assembly body (20) further supports a second drive system in the form of a firing drive system (40) configured to apply firing motions to corresponding portions of interchangeable shaft assembly (14) and its end effector (16). In the present example, firing drive system (40) employs an electric motor (42) that is housed within pistol grip (22) of handle assembly (12) and is operatively coupled with end effector (16), as described below. Electric motor (42) may be of any suitable type, such as a DC brushed motor, a brushless motor, a cordless motor, a synchronous motor, a stepper motor, or any other suitable type of electric motor. Electric motor (42) is powered by a power source shown in the form of a power pack (44) removably coupled to a proximal portion of handle assembly body (20). Power pack (44) includes one or more batteries (not shown) of any suitable type, and may be rechargeable or replaceable.

As seen in FIG. 4, electric motor (42) is electrically coupled to and controlled by a circuit board (46) supported by handle frame (26) within handle assembly body (20). Circuit board (46) may include a microcontroller and is configured to direct power from power pack (44) to electric motor (42) and thereby energize motor (42) to fire end effector (16). Electric motor (42) is configured to interface with a drive gear arrangement (not shown) that is operable to actuate an elongate drive member (48) axially relative to handle frame (26) in response to activation of motor (42). As seen best in FIG. 5, a distal end of drive member (48) is exposed through a distal opening of handle assembly (12) and is configured to couple to a translating member of shaft assembly (14) to thereby operatively couple motor (42) with end effector (16), as described below.

Electric motor (42) is energized by battery pack (44) in response to actuation of a firing trigger (50), which is pivotally supported by handle assembly (12) as best seen in FIGS. 3A and 3B. In the present example, firing trigger (50) is positioned "outboard" of closure trigger (24). Similar to closure trigger (24), firing trigger (50) is configured to be squeezed by the clinician toward pistol grip (22) from an unactuated position (FIG. 3B) to an actuated position (not shown). Firing trigger (50) may be biased toward the unactuated position by a resilient member (not shown). When firing trigger (50) is depressed from the unactuated position to the actuated position, firing trigger (50) causes battery pack (44) to energize motor (42) to actuate drive member (48) longitudinally and thereby fire end effector (16). As shown in FIGS. 3A and 3B, handle assembly (12) further includes a firing trigger safety button (52) that is selectively pivotable between a safety position and a firing position to prevent inadvertent actuation of firing trigger (50).

Figure 5:
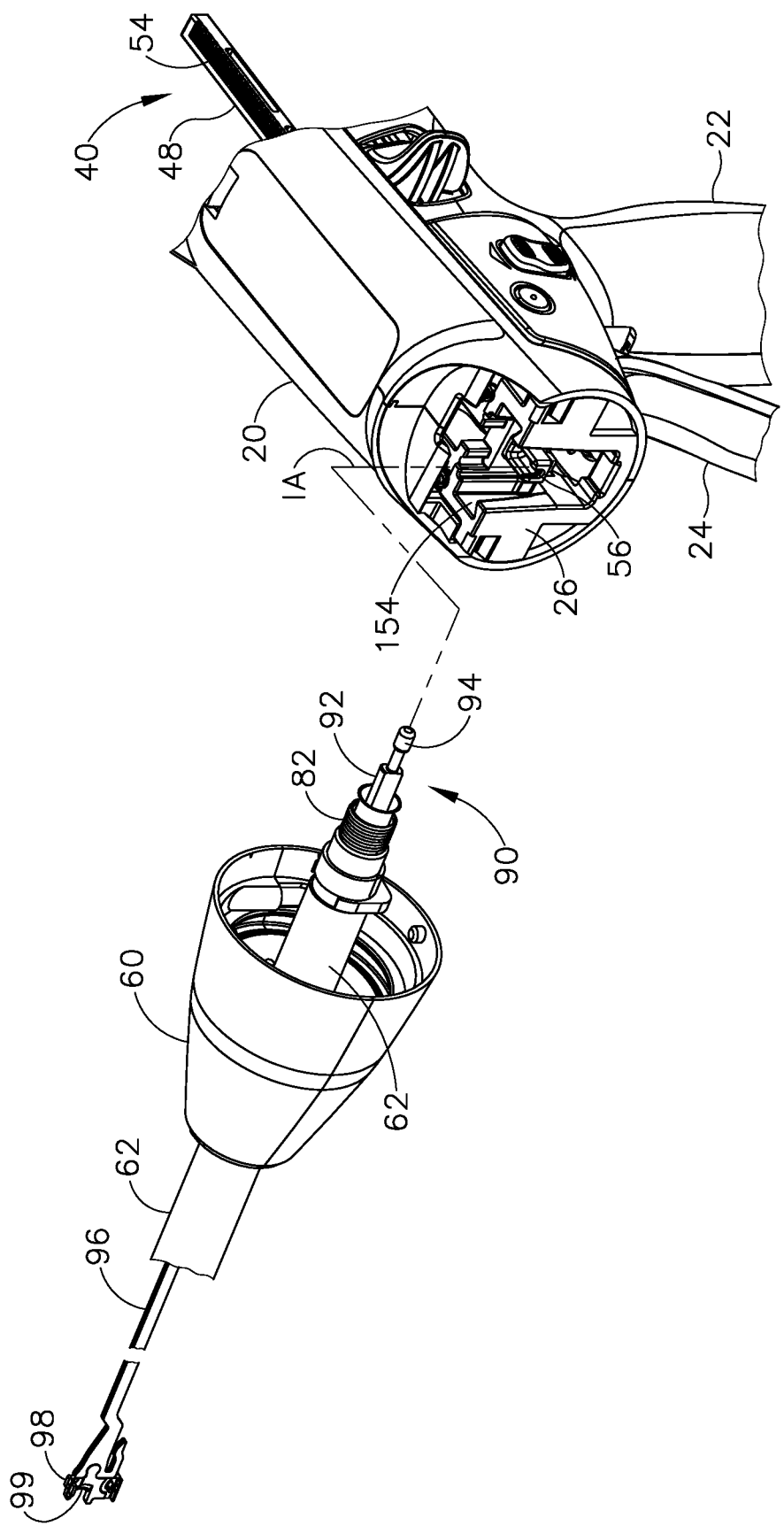
FIG. 5 depicts another perspective view of the surgical instrument of FIG. 1 in a separated state, with certain components of the handle assembly and the shaft assembly omitted to reveal components of a firing system.

As shown best in FIG. 5, elongate drive member (48) of firing drive system (40) includes a rack of teeth (54) formed on at least a proximal portion thereof for meshing engagement with a corresponding drive gear arrangement (not shown) that interfaces with electric motor (42). Drive member (48) further includes an attachment cradle (56) on a distal end thereof, which is configured to receive and couple with an elongate translating member of shaft assembly (14), described below. Drive member (48) is configured to con- figured to be driven by motor (42) from a proximal position to a distal position to thereby actuate the translating member of shaft assembly (14) and fire end effector (16).

B. Interchangeable Shaft Assembly of Surgical Stapling Instrument

As shown in FIGS. 1-2, interchangeable shaft assembly (14) of the present example includes a proximal nozzle (60), an elongate proximal closure tube (62) extending distally from nozzle (60), an articulation joint (64) disposed at a distal end of the closure tube (62), a distal closure tube segment (66) coupled to a distal end of articulation joint (64), and end effector (16) extending distally therefrom.

End effector (16) includes a first jaw comprising an elongate channel (70) that receives a cartridge (72), and a second jaw comprising an anvil (74) configured to pivot relative to channel (70) between open and closed positions for clamping tissue between anvil (74) and cartridge (72). Cartridge (72) is shown in the form of a conventional staple cartridge having features described in greater detail below, and is configured to fire a plurality of staples into tissue clamped by end effector (16). In other examples, end effector (16) may be suitably configured to apply a variety of other types of motions and energies to tissue captured by end effector (16), such as radio frequency (RF) energy and/or ultrasonic energy, for example. For instance, cartridge (72) may be configured to apply RF to tissue as generally disclosed in U.S. application Ser. No. 15/636,096, entitled "Surgical System Couplable With Staple Cartridge And Radio Frequency Cartridge, And Method Of Using Same," filed Jun. 28, 2017, the disclosure of which is incorporated by reference herein.

Anvil (74) of end effector (16) is operatively coupled with closure drive system (30) of handle assembly (12), and is configured to pivot between open and closed positions, about a pivot axis that extends transversely to shaft axis (SA), in response to actuation of closure trigger (24). In particular, anvil (74) is configured to as assume an open position when closure trigger (24) is in the unactuated position, and a closed position when closure trigger (24) depressed to the actuated position. Anvil (74) is coupled with closure drive system (30) via proximal closure tube (62) and distal closure tube segment (66), among other components described below. Proximal closure tube (62) and distal closure tube segment (66) are configured to translate proximally and distally relative to nozzle (60) to thereby actuate anvil (74) about its pivot axis in response to actuation of closure trigger (24).

Articulation joint (64) is configured to provide articulation of end effector (16) relative to proximal closure tube (62) and corresponding components of shaft assembly (14) about an articulation axis (AA) that extends transversely to shaft axis (SA). In some examples, end effector (16) may be articulated to a desired orientation by pushing end effector (16) against soft tissue and/or bone within the patient. In other examples, end effector (16) may be articulated by an articulation driver (not shown).

As best seen in FIG. 4, nozzle (60) of interchangeable shaft assembly (14) houses a tool chassis (80) that rotatably supports nozzle (60). Nozzle (60) and end effector (16) are configured to rotate relative to tool chassis (80) about shaft axis (SA), as indicated in FIG. 1. As shown in FIG. 5, proximal closure tube (62) houses an internal spine (82) that is rotatably supported by tool chassis (80) (omitted from view in FIG. 5) at a proximal end and is coupled to end effector (16) at a distal end. Tool chassis (80) further supports a closure shuttle (84) that is configured to translate proximally and distally relative to tool chassis (80). A distal end of closure shuttle (84) is coupled to and rotatably supports a proximal end of proximal closure tube (62). A proximal end of closure shuttle (84) includes a pair of proximally extending hooks (86) configured to couple with closure drive system (30) of handle assembly (12). In particular, hooks (86) are configured to releasably capture attachment pin (34) of closure drive system (30) when interchangeable shaft assembly (14) is coupled with handle assembly (12). Accordingly, actuation of closure trigger (24) to the actuated position (see FIG. 3B) drives closure shuttle (84) distally, which in turn drives proximal closure tube (62) and distal closure tube segment (66) distally, thereby actuating anvil (74) to a closed position for clamping tissue with end effector (16). Returning trigger to the unactuated position (see FIG. 3A) actuates these components proximally, thereby returning anvil (74) to an open position.

As seen best in FIG. 5, interchangeable shaft assembly (14) further includes an internal firing system (90) configured to operatively couple with firing drive system (40) of handle assembly (12) when shaft assembly (14) is coupled to handle assembly (12). Firing system (90) includes an intermediate firing shaft (92) slidably received within spine (82) and proximal closure tube (62). Intermediate firing shaft (92) includes a proximal end having an attachment lug (94) configured to rotatably seat within attachment cradle (56) of drive member (48) of firing drive system (40), and a distal end configured to couple to an elongate knife bar (96). Knife bar (96) is connected at its distal end to a knife member (98), which includes a sharpened cutting edge (99) configured to sever tissue clamped by end effector (16) as knife member advances distally through staple cartridge (72). Accordingly, actuation of firing trigger (50) actuates drive member (48) distally, which in turn drives intermediate firing shaft (92), knife bar (96), and knife member (98) distally to thereby cut tissue and simultaneously fire staple cartridge (72), as described below. Knife member (98) may include one or more anvil engagement features configured to engage and maintain anvil (74) in a closed state throughout cutting and stapling of tissue.

Figure 6:
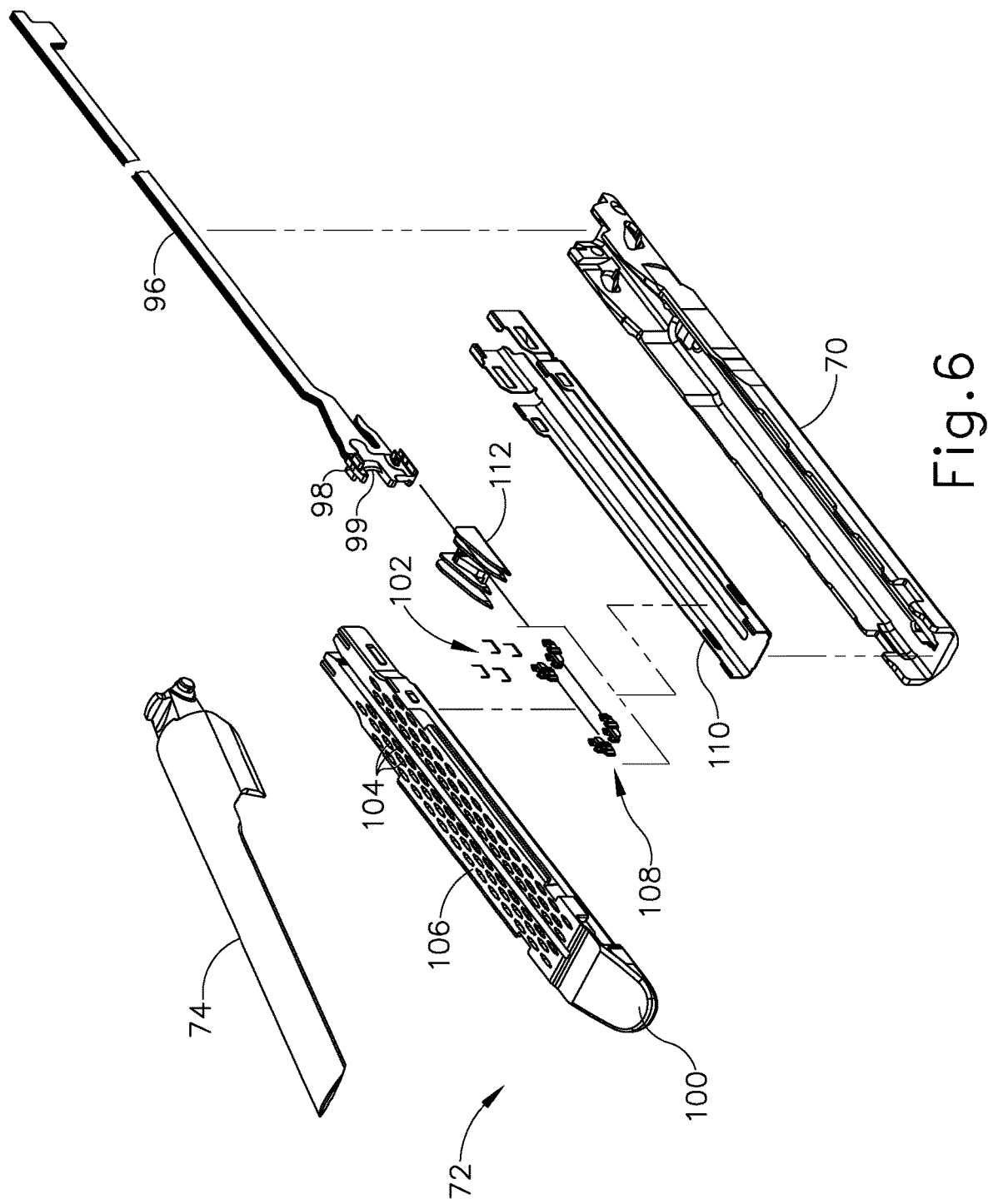
FIG. 6 depicts an exploded perspective view of an end effector of the surgical instrument of FIG. 1, in combination with certain components of the firing system.

As seen best in FIG. 6, staple cartridge (72) includes a molded cartridge body (100) that houses a plurality of staples (102) within staple cavities (104) that open upwardly through a staple deck (106) of cartridge body (100). A plurality of staple drivers (108) are positioned within staple cavities (104), beneath staples (102). A cartridge tray (110) covers an open bottom side of cartridge body (100) and holds together the various components of staple cartridge (72). A wedge sled (112) is slidably received within slots formed in cartridge body (100), and is driven distally by knife member (98) upon actuation of firing drive system (40). As wedge sled (112) advances distally through staple cartridge (72), wedge sled (112) cams staple drivers (108) upwardly to thereby drive staples (102) through tissue clamped by anvil (74) and into staple forming pockets (not shown) formed in anvil (74), thereby deforming staples (102). Simultaneously, cutting edge (99) of knife member (98) severs the tissue clamped in end effector (16). After firing staple cartridge (72), knife member (98) may be retracted to a proximal position to thereby permit opening of anvil (74) and release of the stapled/severed tissue.

C. Electrical Connections within Surgical Instrument

Interchangeable shaft assembly (14) and variations thereof that are suitable for use with handle assembly (12) may employ one or more sensors and/or various other electrical components that require electrical communication with handle circuit board (46) of handle assembly (12). For instance, a proximal portion of shaft assembly (14) and/or end effector (16) may include one more sensors (see e.g., FIG. 8) and/or one or more RF electrodes (not shown) configured to electrically couple with handle circuit board (46) to enable operation thereof. As described below, shaft assembly (14) is suitably configured to enable rotation of end effector (16), among other components of shaft assembly (14), relative to handle assembly (12) while maintaining electrical coupling between shaft assembly (14) and handle assembly (12).

Figure 7:
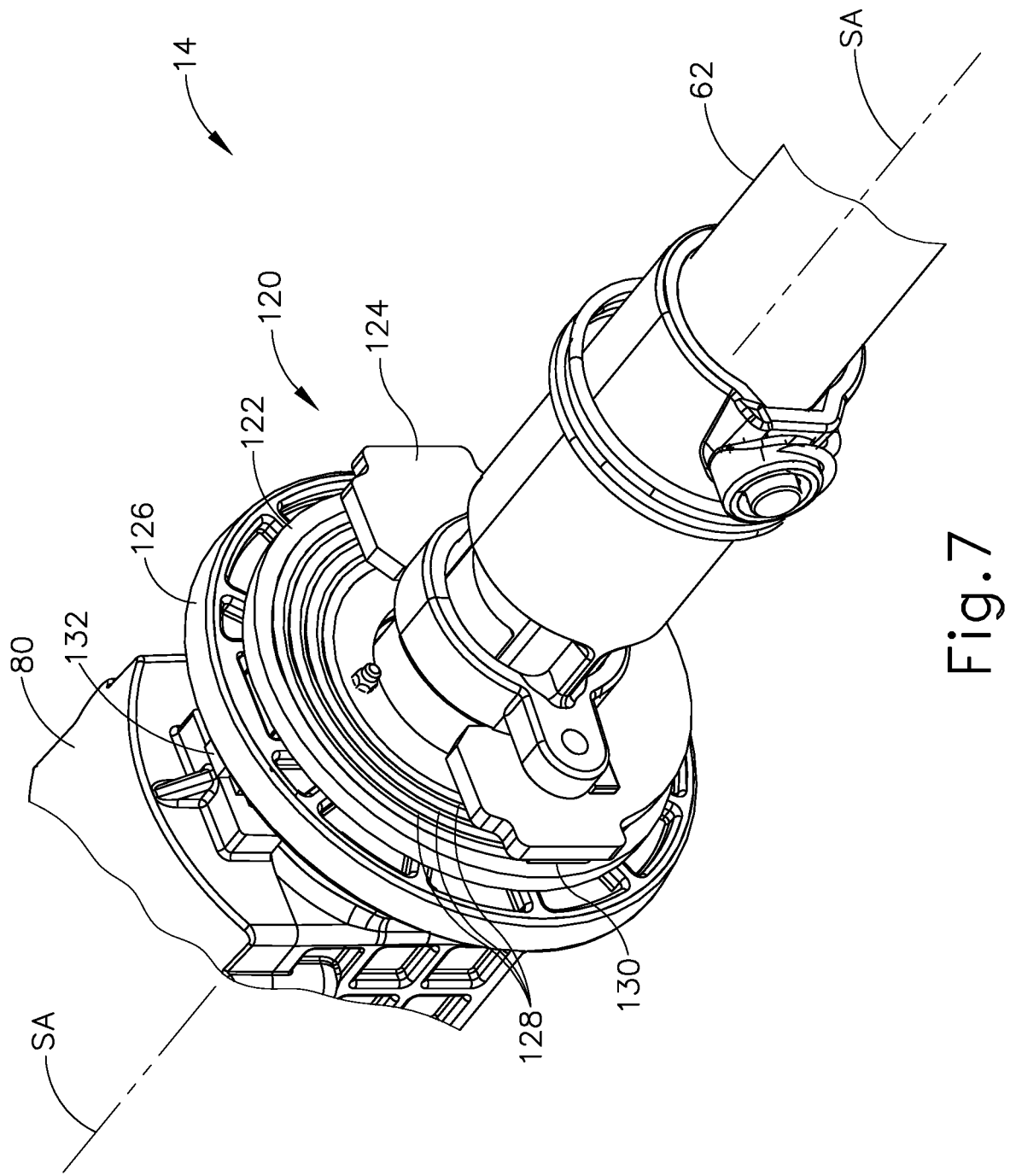
FIG. 7 depicts a perspective view of a proximal portion of the interchangeable shaft assembly of the surgical instrument of FIG. 1, with a nozzle of the shaft assembly omitted to reveal details of an internal slip ring assembly.

As shown in FIG. 7, interchangeable shaft assembly (14) further includes a slip ring assembly (120) housed within nozzle (60) and configured to electrically couple shaft assembly (14) with handle assembly (12) for communication of electrical power and/or sensor signals between end effector (16) and handle circuit board (46). Slip ring assembly (120) is configured to provide such electrical communication while facilitating rotation of nozzle (60) and end effector (16), among other rotating components of shaft assembly (14), relative to tool chassis (80) and handle assembly (12) about shaft axis (SA). Slip ring assembly (120) comprises a proximal connector flange (122) mounted to a chassis flange (126) that extends distally from tool chassis (80), and a distal connector flange (124) secured to an interior of nozzle (60). Distal connector flange (124) is configured to rotate with nozzle (60) relative to tool chassis (80) and chassis flange (126). Accordingly, the proximal face of distal connector flange (124) confronts and is configured to rotate relative to a distal face of proximal connector flange (122) about shaft axis (SA).

The distal face of proximal connector flange (122) of slip ring assembly (120) includes a plurality of annular conductors (128) arranged substantially concentrically. The proximal face of distal connector flange (124) supports one or more electrical coupling members (130) each supporting a plurality of electrical contacts (not shown). Each electrical contact is positioned to contact a respective annular conductor (128) of proximal connector flange (122). Such an arrangement permits relative rotation between proximal connector flange (122) and distal connector flange (124) while maintaining electrical contact therebetween. Proximal connector flange (122) includes an electrical connector (132) extending proximally from a proximal face of proximal connector flange (122). Electrical connector (132) is configured to electrically couple annular conductors (128) with a shaft circuit board (134), shown schematically in FIG. 4, which may be mounted to shaft chassis (80) and include a microcontroller.

D. Attachment of Interchangeable Shaft Assembly to Handle Assembly

As described in greater detail below, interchangeable shaft assembly (14) is configured to be releasably coupled with handle assembly (12). It will be appreciated that various other types of interchangeable shaft assemblies having end effectors configured for various types of surgical procedures may be used in combination with handle assembly (12) described above.

As shown best in FIG. 4, a proximal end of tool chassis (80) of interchangeable shaft assembly (14) includes a pair of tapered attachment members (150) extending transversely to shaft axis (SA), and a shaft-side electrical connector (152) positioned therebetween. Shaft electrical connector (152) is in electrical communication with shaft circuit board (134) of shaft assembly (14). A distal end of handle frame (26) of handle assembly (12) includes a pair of dovetail receiving slots (154), and a handle-side electrical connector (156) arranged therebetween. Handle electrical connector (156) is in electrical communication with handle circuit board (46) of handle assembly (12). During attachment of shaft assembly (14) to handle assembly (12), as described below, tapered attachment members (150) are received within dovetail receiving slots (154) along an installation axis (IA) that is transverse to shaft axis (SA). Additionally, shaft electrical connector (152) is electrically coupled with handle electrical connector (156) when handle assembly (12) and interchangeable shaft assembly (14) are suitably coupled in accordance with the teachings herein. The proximal end of interchangeable shaft assembly (14) additionally includes a latch assembly (158) configured to releasably latch tool chassis (80) to handle frame (26) of handle assembly (12) when shaft assembly (14) is coupled with handle assembly (12).

As shown in FIG. 4, to attach interchangeable shaft assembly (14) to handle assembly (12), the clinician first aligns tapered attachment members (150) of tool chassis (80) with dovetail receiving slots (154) of handle frame (26). The clinician then moves shaft assembly (14) toward handle assembly (12) along installation axis (IA), thereby seating tapered attachment members (150) within dovetail receiving slots (154) and lockingly engaging latch assembly (158) with a distal portion of handle assembly (12). In doing so, attachment lug (94) of intermediate firing shaft (92) is also seated within cradle (56) of longitudinally movable drive member (48), thereby operatively coupling firing system (90) of shaft assembly (14) with firing drive system (40) of handle assembly (12). Additionally, proximal hooks (86) of closure shuttle (84) slide over and capture opposed lateral ends of attachment pin (34) extending from closure link (32), thereby operatively coupling the anvil closure components of shaft assembly (14) with closure drive system (30) of handle assembly (12). Additionally, during attachment of shaft assembly (14) with handle assembly (12), shaft electrical connector (152) on tool chassis (80) is electrically coupled with handle electrical connector (156) on handle frame (26), thereby placing shaft circuit board (134) of shaft assembly (14) in electrical communication with handle circuit board (46) of handle assembly (12).

In various examples, surgical instrument (10) may be further configured in accordance with one or more teachings of U.S. Pat. No. 9,345,481, entitled "Staple Cartridge Tissue Thickness Sensor System," issued May 24, 2016; U.S. Pat. No. 8,608,045, entitled "Powered Surgical Cutting and Stapling Apparatus With Manually Retractable Firing System," issued Dec. 17, 2013; U.S. application Ser. No. 15/635,663, entitled "Method For Articulating A Surgical Instrument," filed Jun. 28, 2017; U.S. application Ser. No. 15/635,631, entitled "Surgical Instrument With Axially Moveable Closure Member," filed Jun. 28, 2017; U.S. application Ser. No. 15/635,837, entitled "Surgical Instrument Comprising An Articulation System Lockable To A Frame," filed Jun. 28, 2017; U.S. Pat. Pub. No. 2016/0066911, entitled "Smart Cartridge Wake Up Operation And Data Retention," published Mar. 10, 2016; U.S. Pat. Pub. No. 2015/0272575, entitled "Surgical Instrument Comprising A Sensor System," published Oct. 1, 2015; U.S. Pat. Pub. No. 2014/0263552, entitled "Staple Cartridge Tissue Thickness Sensor System," published Sep. 18, 2014; and/or U.S. Pat. Pub. No. 2014/0263541, entitled "Articulatable Surgical Instrument Comprising An Articulation Lock," published Sep. 18, 2014, the disclosures of which are incorporated by reference herein.

E. Exemplary End Effector with Sensors

In some instances, it may be desirable to provide the end effector of a surgical instrument with one or more sensors for sensing various operating conditions of the end effector. Such sensed conditions can then be communicated as electrical signals to a controller of the surgical instrument, such as a controller of shaft circuit board (134) and/or handle circuit board (46) of instrument (10) described above. The controller(s) may then take one or more actions in response to receiving such signals, such as providing one or more indications to the clinician operating the instrument.

Figure 8:
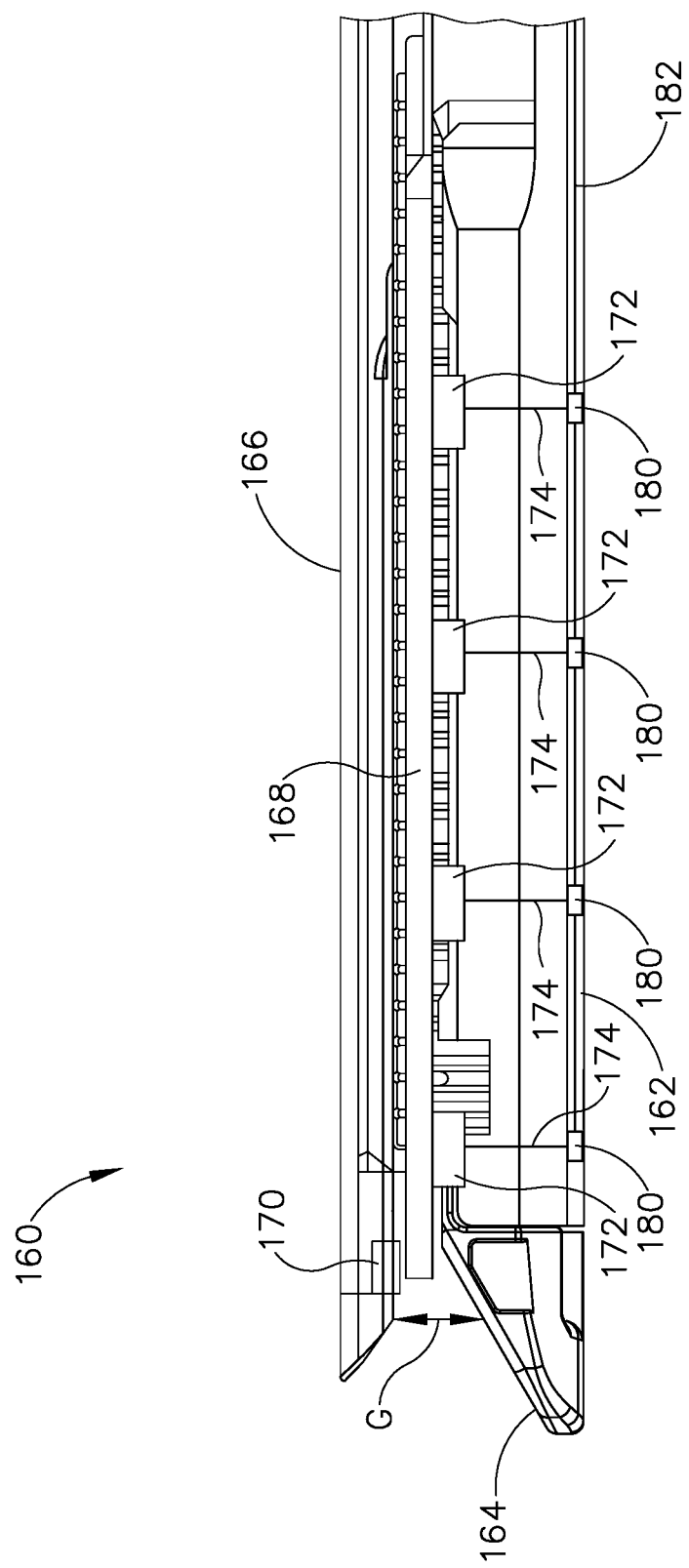
FIG. 8 depicts a side elevational view of another exemplary end effector having a plurality of sensors.

FIG. 8 illustrates an exemplary alternative end effector (160) suitable for use with surgical instrument (10) described above. End effector (160) is similar to end effector (16) described above in that end effector (160) includes a first jaw comprising an elongate channel (162) that receives a staple cartridge (164), and a second jaw comprising an anvil (166) configured to pivot relative to channel (162) between open and closed positions for clamping tissue (168) between anvil (166) and staple cartridge (164). Staple cartridge (164) may be similar to staple cartridge (72) described above.

End effector (160) differs from end effector (16) in that end effector (160) includes a first sensor (170) disposed on a tissue clamping side of anvil (166), and a plurality of second sensors (172) spaced along a length of channel (162). In other versions, one or more sensors, such as one or more of second sensors (172), may be provided on staple cartridge (164). In the present example, first sensor (170) is configured to detect one or more conditions of end effector (160), such as a gap (G) between anvil (166) and staple cartridge (164), which may correspond to a thickness of tissue (168) clamped by end effector (160). Second sensors (172) are also configured to detect one or more conditions of end effector (160) and/or of tissue (168) clamped by end effector (160). For instance, second sensors (172) may be configured to detect one or more conditions such as a color of staple cartridge (164), a length of staple cartridge (164), a clamping condition of end effector (160), and/or the number of actual and/or remaining uses of end effector (160) and/or staple cartridge (164), for example. While end effector (160) is shown having one first sensor (160) and four second sensors (172), various other suitable quantities and arrangements of sensors (170, 172) may be provided in other examples.

Each sensor (170, 172) may comprise any sensor type suitable for measuring the respective one or more conditions of end effector (160). For instance, each sensor (170, 172) may comprise a magnetic sensor (e.g., a Hall effect sensor), a strain gauge, a pressure sensor, an inductive sensor (e.g., an eddy current sensor), a resistive sensor, a capacitive sensor, or an optical sensor, for example. Each sensor (170, 172) is configured to communicate electrical signals corresponding to a sensed condition of end effector (160) to shaft circuit board (134), which may in turn communicate information based on the signals to handle circuit board (46), via slip ring assembly (120) described above.

It should be understood that channel (162) may selectively receive staple cartridge (164) such that staple cartridge (164) may be attached to channel (162), used in accordance with the description herein, removed from channel (162), and replaced with an unused, second staple cartridge (164). Therefore, sensors (172) associated with staple cartridge (164) may be configured to selectively establish an electrical connection with shaft circuit board (134) once staple cartridge (164) is suitably coupled to channel (162). In the current example, second sensors (172) each include an electrical contact (174), while channel (162) includes a plurality of electrical contacts (180). Corresponding contacts (174, 180) are dimensioned to electrically couple with each other when staple cartridge (164) is suitably coupled with channel (162). Additionally, channel (162) includes electrical traces (182) extending from contacts (180) all the way to electrical coupling member (130) of slip ring assembly (120). Therefore, when staple cartridge (164) is suitably coupled with channel (162), second sensors (172) are in electrical communication with shaft circuit board (134).

While sensors (172) are attached to staple cartridge (164) in the present example, any other type of electrically activated components may be used in addition to, or in replacement of, sensors (172). For example, one or more sensors (172) may be replaced with one or more elements designed to deliver electrical therapeutic energy to tissue captured within end effector (160), such as a pad that transmits Radio Frequency (RF) energy to tissue.

II. EXEMPLARY CARTRIDGES AND CHANNELS WITH CAPACITIVE ELECTRICAL INTERFACE

As described above, second sensors (172) associated with staple cartridge (164) are configured to couple with shaft circuit board (134) via contacts (174, 180) and electrical tracing (182) when staple cartridge (164) is suitably coupled with channel (162). As also described above, shaft circuit board (134) may be powered by power pack (44) when interchangeable shaft assembly (14) is suitably coupled with handle assembly (12). Therefore, when handle assembly (12) and interchangeable shaft assembly (14) are suitably coupled while power pack (44) is powering handle assembly (12), power pack (44) is also in electrical communication with contacts (180) located along channel (162).

As also described above, staple cartridge (164) is dimensioned to selectively couple with channel (162) such that a first staple cartridge (164) may be used in accordance with the teachings herein, then be removed from channel (162), and then be replaced with an unused, second staple cartridge (164). Between removing a first staple cartridge (164) from channel (162) and coupling a second staple cartridge (164) with channel (162), an operator may dip the distal end of shaft assembly (14), including channel (162), into a saline solution to clean shaft assembly (14) for another use during the same surgical procedure. Additionally, during exemplary use, saline solutions, bodily fluids, and/or other fluids may accumulate within channel (162) and cartridge (164). Accumulation of such fluids may interfere with the electrical connection between corresponding contacts (174, 180), adversely affecting the electrical connection between corresponding contacts (174, 180). Additionally, accumulation of such bodily fluids may interfere with specific contacts (174, 180), creating an undesirable short circuit.

It may therefore be desirable to provide a cartridge and/or channel assembly that may help prevent undesirable short circuits or other interferences with electrical connections (174, 180) via exposure to various fluids. While various examples of cartridges and channels are described below, it should be understood various combinations or modifications may be made to such cartridges and channels as would be apparent to one having ordinary skill in the art in view of the teachings herein.

Figure 9:
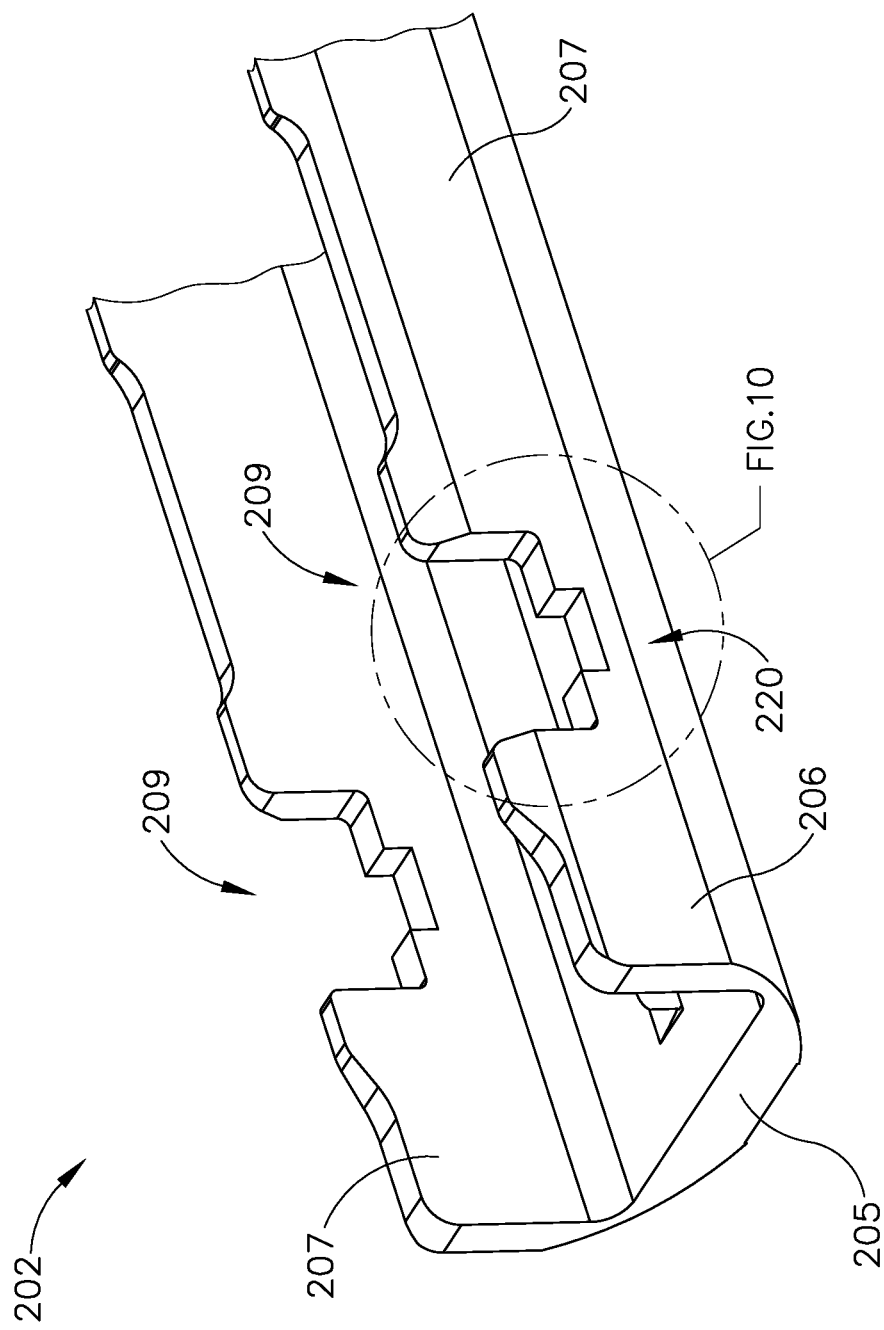
FIG. 9 depicts a perspective view of an exemplary elongate channel that may be readily incorporated into the end effector of FIG. 8.

FIGS. 9-11 shows an exemplary alternative elongate channel (202) that may be readily incorporated into end effector (160) described above in replacement of elongate channel (162); while FIG. 11 shows an exemplary staple cartridge (204) that may selective couple with elongate channel (202) to form an exemplary cartridge and channel assembly (200). Channel (202) and cartridge (204) are substantially similar to channel (162) and cartridge (164) described above, respectively, with differences elaborated below. As will be described in greater detail below, channel (202) includes a channel contact assembly (220) configured to electrically couple with a cartridge contact assembly (210). As will also be described in greater detail below, contact assemblies (210, 220) electrically couple forming a capacitor having a dielectric material between two conductive plates (212, 222); where the dialectical material may also protect at least one conductive plate (212, 222) of contact assemblies (210, 220) to help prevent fluid from creating a short circuit.

As best shown in FIG. 11, staple cartridge (204) includes a cartridge body (208), and a cartridge contact assembly (210). Cartridge contact assembly (210) includes a conductive plate (212) and an electrically activated component (214) electrically coupled with conductive plate (212) via an electrical connection (216). Conductive plate (212) is located on a laterally extending lug of cartridge body (208). As will be described in greater detail below, conductive plate (212) is configured to form a capacitor with portions of channel contact assembly (220) in order to power electrically activated component (214).

Channel (202) includes a channel body (206) and a channel contact assembly (220). Channel body (206) includes a pair of side walls (207) connected to lateral ends of a base wall (205). Each side wall (207) defines a recess (209), with each recess (209) housing a separate channel contact assembly (220). Channel body (206) is dimensioned to selectively couple with cartridge (204). Recess (209) houses a portion of channel contact assembly (220) such that channel contact assembly (220) may electrically couple with cartridge contact assembly (210) when cartridge (204) is suitably coupled with channel (202).

In the current example, one channel contact assembly (220) on one side wall (207) is a "hot" contact assembly, while the other contact assembly (220) is a "return" contact assembly such that when cartridge (204) is suitably coupled with channel (202), cartridge (204) and each contact assembly (220) complete an electrical circuit in order to power electrically activated component (214). Therefore, electrically activated components (214) in the current example is in electrical communication with two conductive plates (212) on opposite lateral sides of cartridge body (208) via two electrical connectors (216).

While the current example has one contact assembly (220) on each side wall (207), any suitably number of contact assemblies (220) may be used as would be apparent to one having ordinary skill in the art in view of the teachings herein. It should also be understood that the number of cartridge contact assemblies (210) may correspond with the number of channel contact assemblies (220). Therefore, various electrically activated components (214) may be incorporated into cartridge (204). While the current contact assemblies (220) are associated with side walls (207), contact assemblies (220) may be associated along any other suitable portion of channel (202) as would be apparent to one having ordinary skill in the art in view of the teachings herein.

Channel contact assembly (220) includes a conductive plate (222), an electrical trace or lead (224), and a dielectric cover (226). Electrical trace or lead (224) extends from conductive plate (222) to shaft circuit board (134). Because electrical trace or lead (224) extends from conductive plate (222) to shaft circuit board (134), power pack (44) may power conductive plate (222) when shaft assembly (14) is suitably coupled with handle assembly (12). In other words, conductive plate (222) may be electrically charged by power pack (44).

Conductive plate (222) is housed within an extended cavity (228) defined by side wall (207) and dielectric cover (226). Conductive plate (222) is directly adjacent to dielectric cover (226). When cartridge (204) is suitably coupled with channel (202), conductive plate (212) is directly adjacent to dielectric cover (226). Therefore, dielectric cover (226) acts as a dielectric material between conductive plates (212, 222) when cartridge (204) is suitably coupled with channel (202) such that dielectric cover (226) and conductive plates (212, 222) form a capacitor. Because conductive plate (212) is electrically charged by battery pack (44), current may travel through the capacitor formed by conductive plates (212, 222) and dielectric cover (226) in order to power electrically activated component (214). Battery pack (44) may power electrically activated component (214) via conductive plate (212, 222) and dielectric cover (226) through any suitably means as would be apparent to one having ordinary skill in the art in view of the teachings herein.

Additionally, Dielectric cover (226) acts as a sheath for conductive plate (222) such that accumulated fluid may not come into contact with conductive plate (222). In other words, dielectric cover (226) acts a fluidic barrier between conductive plate (222) within cavity (228) and an outer surface of dielectric cover (226) facing away from conductive plate (222). Therefore, dielectric cover (226) may allow conductive plates (212, 222) to suitably electrically couple with each other to power electrically activated component (214) while preventing fluidic exposure to conductive plates (222). Preventing fluidic exposure to conductive plates (222) may help prevent undesired short circuit connections between hot conductive plates (222) and corresponding return conductive plates (222) (224).

Dielectric cover (226) may be formed of any suitable material as would be apparent to one having ordinary skill in the art in view of the teachings herein. Dielectric cover (226) may be installed over conductive plate (222) utilizing any suitable technique as would be apparent to one having ordinary skill in the art in view of the teachings herein. For example, dielectric cover (226) may be formed of lead zirconate titanate (PZT) wafer that is epoxied over conductive plate (222). Therefore, dielectric cover (226) may include a PZT layer directly adjacent to conductive plate (222) and an epoxy layer place around the PZT layer. Dielectric cover (226) may surround conductive plate (222) such that conductive plate (222) does not need to be housed within cavity (228). For example, a PZT wafer may be placed over conductive plate (222) while an epoxy may surround both PZT wafer and conductive plate (222). While in the current example, dielectric cover (226) is associated with channel contact assembly (220), dielectric cover (226) may associate with cartridge contact assembly (230), both channel contact assembly (220) and cartridge contact assembly (230), or any other suitable arrangement as would be apparent to one having ordinary skill in the art in view of the teachings herein.

Figure 12:
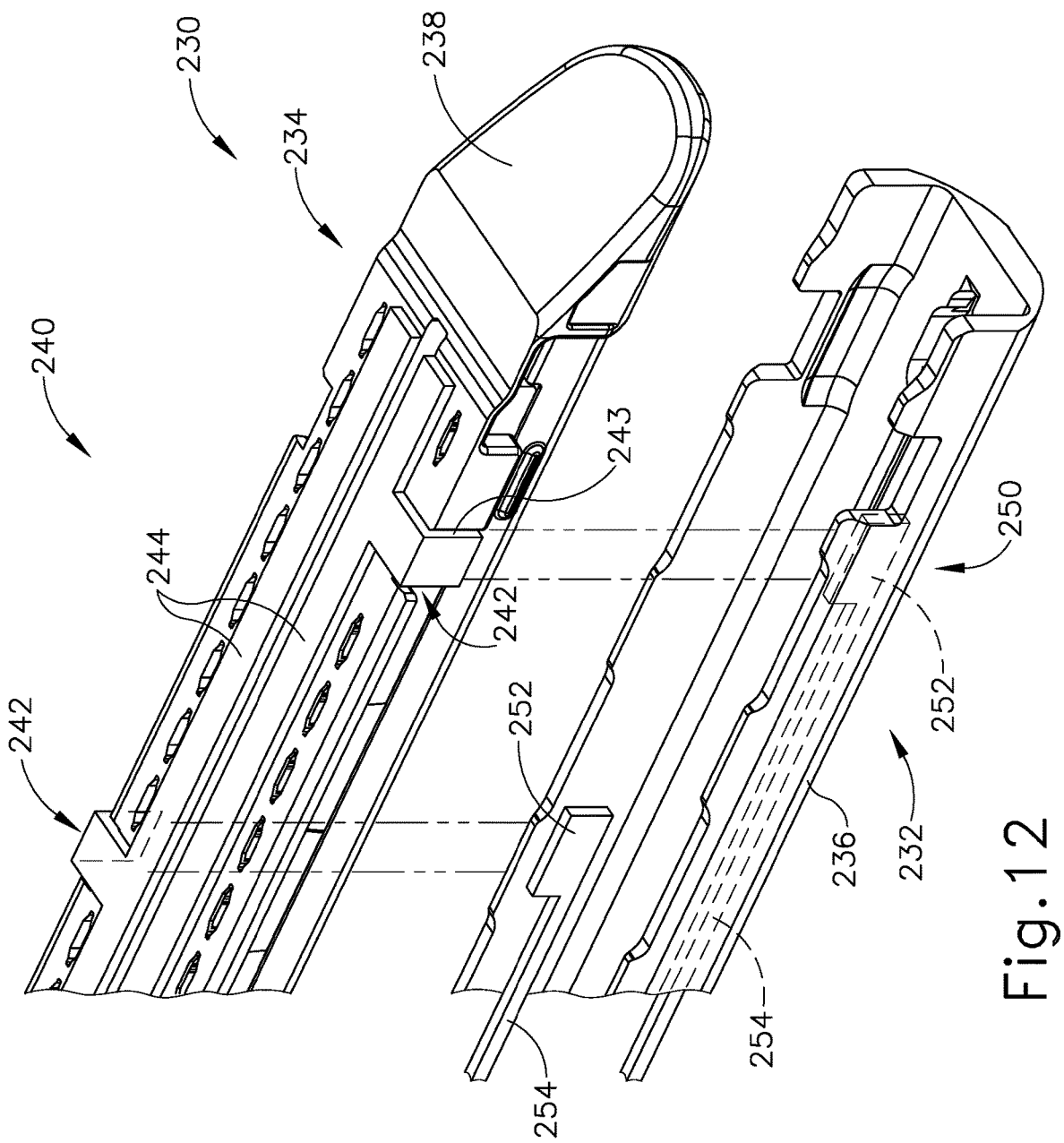
FIG. 12 depicts an exploded perspective view of an exemplary cartridge and channel assembly that may be readily incorporated into the end effector of FIG. 8.
Figure 13B:
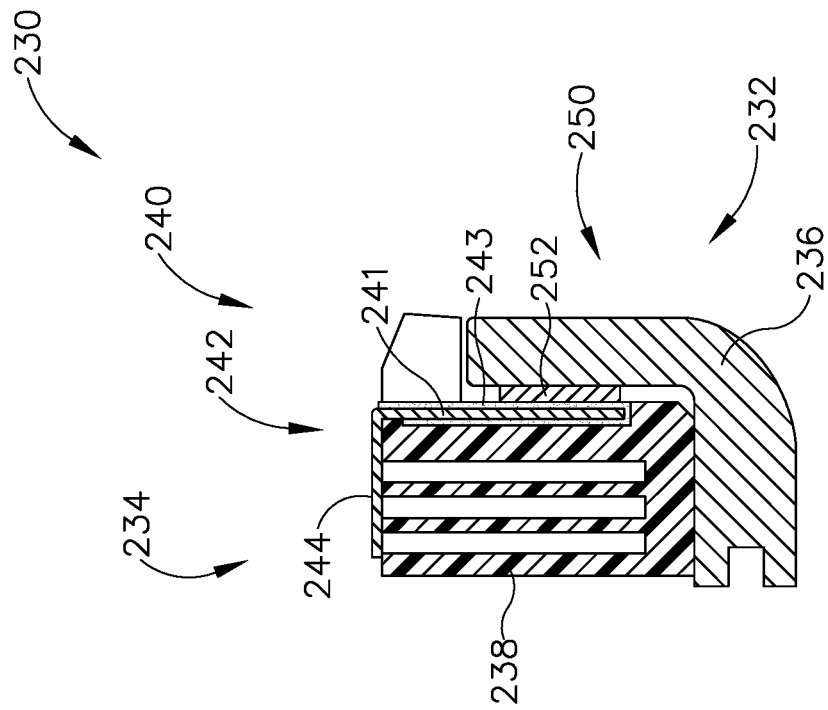
FIG. 13B depicts a cross-sectional end view of the portion of the cartridge and channel assembly of FIG. 12, where the cartridge is coupled with the channel.
Figure 13A:
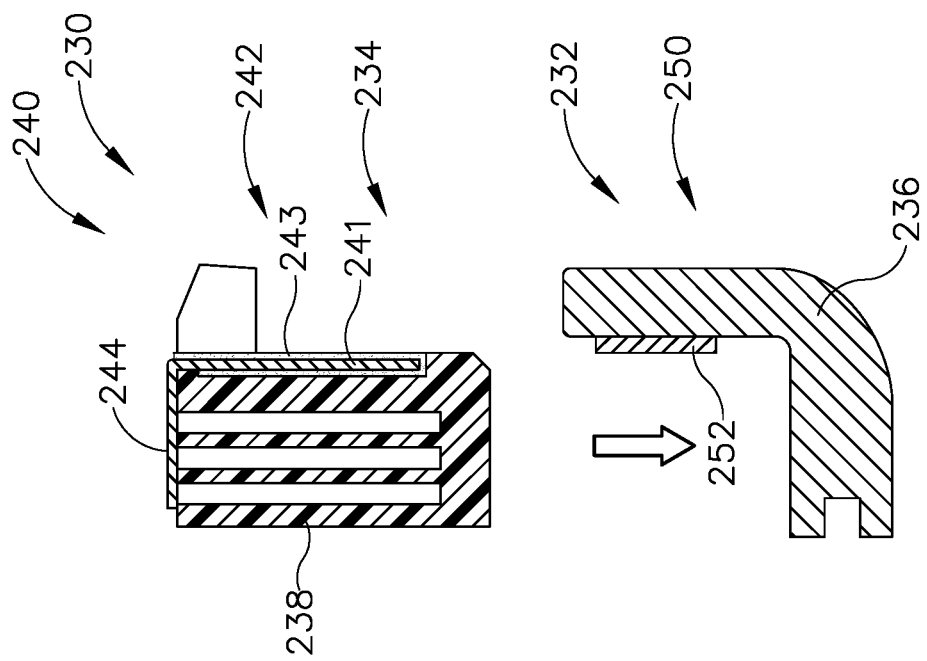
FIG. 13A depicts a cross-sectional end view of a portion of the cartridge and channel assembly of FIG. 12, where the cartridge is decoupled with the channel.

FIGS. 12-13B show an alternative exemplary cartridge and channel assembly (230) that may be readily incorporated into end effector (160) in replacement of cartridge (164) and channel (162), as described above, respectively. Cartridge and channel assembly (230) includes an elongate channel (232) and a staple cartridge (234). Channel (232) and cartridge (234) are substantially similar to channel (162) and cartridge (164) as described above, respectively, with differences elaborated below. FIG. 13A shows cartridge (234) decoupled from channel (232); while FIG. 13B shows cartridge (234) fully coupled with channel (232). As will be described in greater detail below, channel (232) includes a channel contact assembly (250) configured to electrically couple with a cartridge contact assembly (240). As will also be described in greater detail below, contact assemblies (240, 250) electrically couple forming a capacitor having a dielectric material between two conductive plates (242, 252); where the dialectical material may also protect at least one conductive plate (242, 252) of contact assemblies (240, 250) to help prevent fluid from creating a short circuit.

Channel (232) includes a channel body (236) and a channel contact assembly (250). Channel contact assembly (250) includes any suitable number of conductive plates (252) as would be apparent to one having ordinary skill in the art in view of the teachings herein. In the current example, channel contact assembly (250) includes two conductive plates (252) associated with opposite side walls of channel body (236). Channel contact assembly (250) also includes an electrical trace or lead (254) extending from conductive plates (252) to shaft circuit board (134). Because electrical trace or lead (254) extends from conductive plates (252) to shaft circuit board (134), power pack (44) may power conductive plates (252) when shaft assembly (14) is suitably coupled with handle assembly (12). In other words, conductive plates (252) may be electrically charged by power pack (44).

Cartridge (234) includes a cartridge body (238) and a cartridge contact assembly (240). Cartridge contact assembly (240) includes a pair of electrical contacts (242) in electrical communication with an electrically activated component (244) such that one electrical contact (242) is a hot contact and the other electrical contact (242) is a return contact. Electrical contacts (242) are configured to electrically couple with contacts (252) of channel (232) such that power pack (44) may power electrically activated component (244) when shaft assembly (14) is suitably coupled with handle assembly (12).

In the present example, enlarged contact pads (252) are located on opposite side walls of channel body (236). Additionally, enlarged contact pads (252) are located on opposite longitudinal portions of channel body (236), one being proximal and one being distal. Therefore, the increased distance based on the position of enlarged contact pads (252) may help prevent a short circuit from occurring due to fluid bridging the gap between enlarged contact pads (252). Additionally, electrical contacts (242) may include a leaf spring configuration, such that electrical contacts (242) depress when coupled with enlarged contact pads (252), thereby helping ensure the electrical connection between contacts (342, 352).

Electrical contacts (252) include a conductive plate (241) and a dielectric cover (243) surrounding conductive plate (241). Conductive plate (241) is in electrical communication with electrically activated component (244). When cartridge (234) is suitable coupled with channel (2320, conductive plate (252) is directly adjacent to dielectric cover (243). Therefore, dielectric cover (243) acts as a dielectric material between conductive plates (241, 252) when cartridge (234) is suitably coupled with channel (232) such that dielectric cover (243) and conductive plates (241, 252) form a capacitor. Because conductive plate (252) is electrically charged by batter battery pack (44), current may travel through the capacitor formed by conductive plates (241, 252) and dielectric cover (243) in order to power electrically activated component (244). Batter Battery pack (44) may power electrically activate component (244) through any suitable means as would be apparent to one having ordinary skill in the art in view of the teachings herein.

Additionally, dielectric cover (243) acts as a sheath for conductive plate (241) such that accumulated fluid may not come into contact with conductive plate (241). In other words, dielectric cover (243) acts a fluidic barrier for conductive plate (241). Therefore, dielectric cover (243) may allow conductive plates (241, 252) to suitably electrically couple with each other to power electrically activated component (244) while preventing fluidic exposure to conductive plates (241).

Dielectric cover (243) may be formed of any suitable material as would be apparent to one having ordinary skill in the art in view of the teachings herein. Dielectric cover (243) may be installed over conductive plate (241) utilizing any suitable technique as would be apparent to one having ordinary skill in the art in view of the teachings herein. For example, dielectric cover (243) may include a thin layer of polytetrafluoroethylene (PTFE) that is heat shrunk over conductive plate (241). While in the current example, dielectric cover (243) is associated with cartridge contact assembly (240), dielectric cover (243) may associate with channel contact assembly (250), both channel contact assembly (250) and cartridge contact assembly (240), or any other suitable arrangement as would be apparent to one having ordinary skill in the art in view of the teachings herein.

Figure 14:
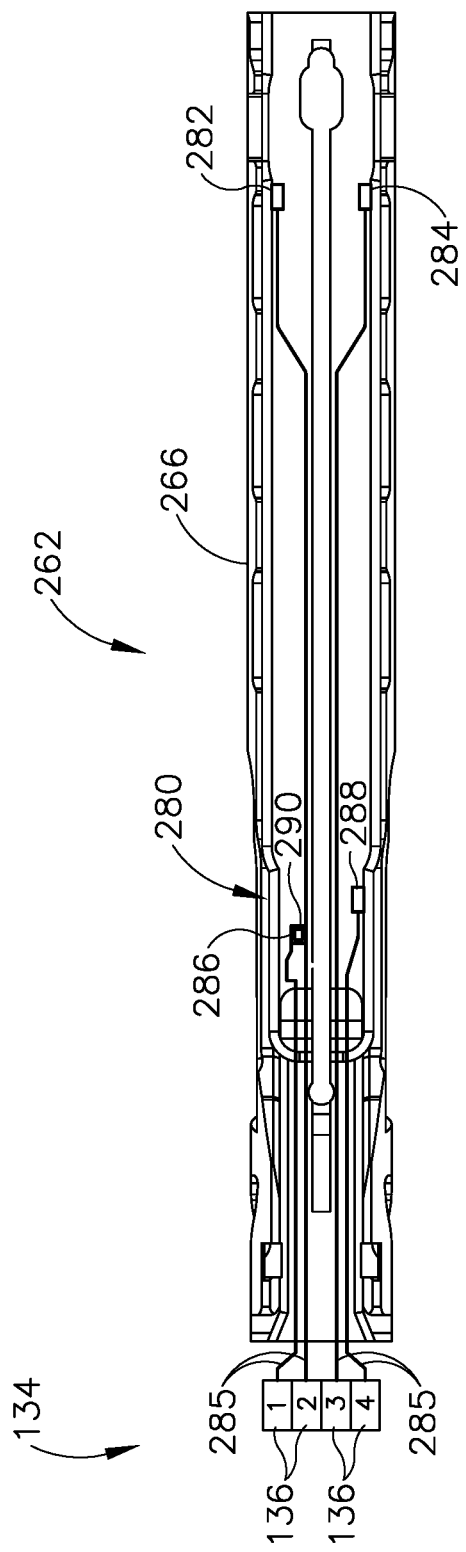
FIG. 14 depicts a schematic view of an alternative elongate channel that may be readily incorporated into the end effector of FIG. 8.
Figure 15:
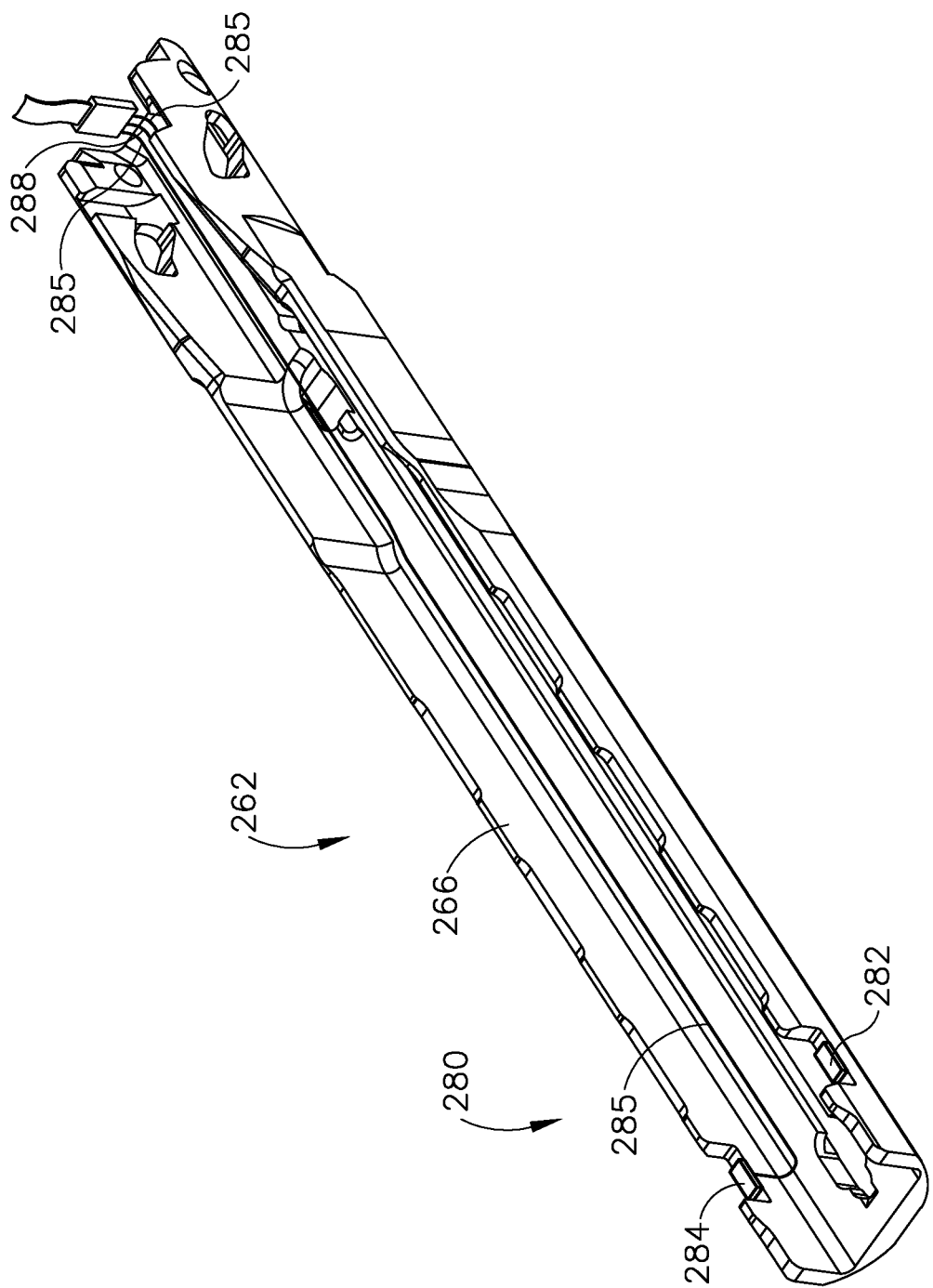
FIG. 15 depicts a perspective view of the elongate channel of FIG. 14.

FIGS. 14 and 15 show an alternative elongate channel (262) that may be readily incorporated into end effector (160) described above, in replacement of elongate channel (162) described above. FIG. 16 shows an alternative staple cartridge (264) that may be readily incorporated into end effector (160) in conjunction with elongate channel (262). Channel (262) and cartridge (264) are substantially similar to channel (162) and cartridge (164) described above, respectively, with differences elaborated below. As will be described in greater detail below, channel (262) includes a channel contact assembly (280) configured to electrically couple with a cartridge contact assembly (270).

As best shown in FIG. 16, staple cartridge (264) includes a cartridge body (268), and a cartridge contact assembly (270). Cartridge body (268) also includes a cartridge pan (269) located at the bottom of cartridge body (268). As will be described in greater detail below, cartridge pan (269) may act as a connector between channel body (266) and for second electrically activated component (278) in order to ground second electrically activated component (278). Cartridge contact assembly (270) includes a first contact (272), a second contact (274), a first electrically activated component (276), a second electrically activated component (278), and electrical connectors (275) connecting contacts (272, 274) with respective electrically activated components (276, 278). Additionally, one electrical connector (275) connects second electrically activated component (278) with pan (269).

As best seen in FIG. 14, channel (262) includes a channel body (266) and a channel contact assembly (280). Channel contact assembly includes a first hot contact (182), a second hot contact (284) a first return contact (186), a second return contact (288), a demodulator (290) coupling first hot contact (282) with first return contact (286), and a plurality of eclectically traces (285). Electrical traces or leads (285) extend from contacts (282, 284, 286, 288) to contacts (136) of shaft circuit board (134). Because electrical trace or lead (224) extends from conductive plate (222) to shaft circuit board (134), power pack (44) may power contacts (282, 284, 286, 288) when shaft assembly (14) is suitably coupled with handle assembly (12). In other words, contacts (282, 284, 286, 288) may be electrically charged by power pack (44). Demodulator (290) may include any suitably parts and may be configured as would be apparent to one having ordinary skill in the art in view of the teachings herein.

When cartridge (264) is suitably coupled with channel (262), first hot contact (282) and first return contact (286) may power first electrically activated component (276) through any suitable means known to one having ordinary skill in the art in view of the teachings herein.

When cartridge (264) is suitably coupled with channel (262), second hot contact (284) may couple with second contact (274) of cartridge (264). Additionally, pan (269) and/or channel body (266) may electrically couple second electrically activated component (278) with ground (288) to thereby complete an electrical circuit. In other words, pan (269) or channel body (266) may be used as a "return" contact to electrically ground second electrically activated component (278), which may save space on channel (262) and/or cartridge (264).

III. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument comprising: (a) a body; (b) a shaft assembly extending distally from the body; (c) an end effector, wherein the end effector comprises: (i) a channel assembly, and (ii) a cartridge assembly configured to selectively couple with the channel assembly, wherein the cartridge assembly comprises an electrically activated component; and (d) an electrical contact assembly configured to electrically couple a power source with the electrically activated component of the cartridge assembly, wherein the electrical contact assembly comprises: (i) a first conductive plate associated with the channel assembly, (ii) a second conductive plate associated with the cartridge assembly, and (iii) a dielectric cover associated with either the first conductive plate or the second conductive plate, wherein the dielectric cover is poisoned between the first conductive plate and the second conductive plate when the cartridge assembly is coupled with the channel assembly.

Example 2

The surgical instrument of Example 1, wherein the dielectric cover comprises a first layer of lead zirconate titanate.

Example 3

The surgical instrument of Example 2, wherein the dielectric cover further comprises an epoxy layer.

Example 4

The surgical instrument of Example 3, wherein the dielectric cover is attached to the first conductive plate.

Example 5

The surgical instrument of any one or more of Examples 1 through 4, wherein the channel assembly defines a recess, wherein the first conductive plate is located within the recess.

Example 6

The surgical instrument of any one or more of Examples 1 through 5, wherein the electrically activated component comprises a sensor.

Example 7

The surgical instrument of any one or more of Examples 1 through 6, wherein the electrically activated component is configured to deliver therapeutic energy to tissue.

Example 8

The surgical instrument of any one or more of Examples 1 through 7, wherein the dielectric cover comprises polytetrafluoroethylene.

Example 9

The surgical instrument of any one or more of Examples 1 through 8, wherein the dielectric cover is heat shrunk over the second conductive plate.

Example 10

The surgical instrument of any one or more of Examples 1 through 9, wherein the second conductive plate comprises a leaf spring configuration.

Example 11

The surgical instrument of any one or more of Examples 1 through 10, further comprising a power source housed within the body, wherein the electrical contact assembly is configured to electrically couple the power source housed within the body with the electrically activated component of the cartridge assembly.

Example 12

The surgical instrument of any one or more of Examples 1 through 11, wherein the channel assembly is configured to electrically ground the second conductive plate when the cartridge assembly is coupled with the channel assembly.

Example 13

The surgical instrument of any one or more of Examples 1 through 12, wherein the shaft assembly comprises a circuit board.

Example 14

The surgical instrument of Example 13, wherein the first conductive plate is in electrical communication with the circuit board.

Example 15

The surgical instrument of Example 14, further comprising an electrical trace extending between the first conductive plate and the circuit board.

Example 16

The surgical instrument of any one or more of Examples 1 through 15, where the end effector further comprises an anvil.

Example 17

The surgical instrument of Example 16, wherein the anvil is configured to pivot relative to the channel assembly from an open position to a closed position.

Example 18

The surgical instrument of any one or more of Examples 1 through 17, wherein the channel assembly comprises a side wall, wherein the first conductive plate is attached to the side wall.

Example 19

A surgical instrument comprising: (a) a body; (b) a shaft assembly extending distally from the body; (c) an end effector, wherein the end effector comprises: (i) a channel assembly, and (ii) a cartridge assembly configured to selectively couple with the channel assembly, wherein the cartridge assembly comprises an electrically activated component; and (d) an electrical contact assembly configured electrically couple a power source with the electrically activated component of the cartridge assembly, wherein the electrical contact assembly comprises a capacitor, wherein the capacitor comprises a first conductive plate, a second conductive plate, and a dielectric cover associated with either the first conductive plate or the second conductive plate, wherein the dielectric cover is poisoned between the first conductive plate and the second conductive plate when the cartridge assembly is coupled with the channel assembly.

Example 20

A surgical instrument comprising: (a) a body; (b) a shaft assembly extending distally from the body; (c) an end effector, wherein the end effector comprises: (i) a channel assembly, and (ii) a cartridge assembly configured to selectively couple with the channel assembly, wherein the cartridge assembly comprises an electrically activated component; and (d) an electrical contact assembly configured electrically couple a power source with the electrically activated component of the cartridge assembly, wherein the electrical contact assembly comprises a capacitor, wherein the capacitor is inoperable when the cartridge assembly is decoupled from the channel assembly, wherein the capacitor is operable when the cartridge assembly is coupled with the channel assembly.

IV. MISCELLANEOUS

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Further, any one or more of the teachings, expressions, embodiments, examples, etc. described herein may be combined with any one or more of the teachings, expressions, embodiments, examples, etc. described in U.S. application. No. 15/934,139, entitled "Surgical Instrument with Compressible Electrical Connector," filed on Mar. 23, 2018, published as U.S. Pub. No. 2019/0290307 on Sep. 26, 2019; U.S. application. No. 15/934,148, entitled "Seal for Surgical Instrument," filed on Mar. 23, 2018, published as U.S. Pub. No. 2019/0290308 on Sep. 26, 2019; U.S. application. No. 15/934,160, entitled "Surgical Instrument with Recessed Contacts and Electrically Insulating Barriers," filed on Mar. 23, 2018, published as U.S. Pub. No. 2019/0290269 on Sep. 26, 2019; U.S. application. No. 15/934,166, entitled "Surgical Instrument with Electrical Contact Under Membrane," filed on Mar. 23, 2018, issued as U.S. Pat. No. 10,631,860 on Apr. 28, 2020; U.S. application. No. 15/934,173, entitled "Staple Cartridge with Short Circuit Prevention Features," filed on Mar. 23, 2018, issued as U.S. Pat. No. 10,639,038 on May 5, 2020; and U.S. application. No. 15/934,190, entitled "Slip Ring Assembly for Surgical Instrument," filed on Mar. 23, 2018, issued as U.S. Pat. No. 10,631,861 on Apr. 28, 2020. The disclosure of each of these applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pat. No. 8,844,789, entitled "Automated End Effector Component Reloading System for Use with a Robotic System," issued Sep. 30, 2014, the disclosure of which is incorporated by reference herein; U.S. Pat. No. 8,820,605, entitled "Robotically-Controlled Surgical Instruments," issued Sep. 2, 2014, the disclosure of which is incorporated by reference herein; U.S. Pat. No. 8,616,431, entitled "Shiftable Drive Interface for Robotically-Controlled Surgical Tool," issued Dec. 31, 2013, the disclosure of which is incorporated by reference herein; U.S. Pat. No. 8,573,461, entitled "Surgical Stapling Instruments with Cam-Driven Staple Deployment Arrangements," issued Nov. 5, 2013, the disclosure of which is incorporated by reference herein; U.S. Pat. No. 8,602,288, entitled "Robotically-Controlled Motorized Surgical End Effector System with Rotary Actuated Closure Systems Having Variable Actuation Speeds," issued Dec. 10, 2013, the disclosure of which is incorporated by reference herein; U.S. Pat. No. 9,301,759, entitled "Robotically-Controlled Surgical Instrument with Selectively Articulatable End Effector," issued Apr. 5, 2016, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. A surgical instrument comprising:
(a) a body;
(b) a shaft assembly extending distally from the body;
(c) an end effector, wherein the end effector comprises:
 (i) a channel assembly, and
 (ii) a cartridge assembly configured to selectively couple with the channel assembly, wherein the cartridge assembly comprises an electrically activated component; and
(d) an electrical contact assembly configured to electrically couple a power source with the electrically activated component of the cartridge assembly, wherein the electrical contact assembly comprises:
 (i) a first conductive plate associated with the channel assembly,
 (ii) a second conductive plate associated with the cartridge assembly, and
 (iii) a dielectric cover associated with either the first conductive plate or the second conductive plate, wherein the dielectric cover is positioned between the first conductive plate and the second conductive plate when the cartridge assembly is coupled with the channel assembly.

2. The surgical instrument of claim 1, wherein the dielectric cover comprises a first layer of lead zirconate titanate.

3. The surgical instrument of claim 2, wherein the dielectric cover further comprises an epoxy layer.

4. The surgical instrument of claim 3, wherein the dielectric cover is attached to the first conductive plate.

5. The surgical instrument of claim 1, wherein the channel assembly defines a recess, wherein the first conductive plate is located within the recess.

6. The surgical instrument of claim 1, wherein the electrically activated component comprises a sensor.

7. The surgical instrument of claim 1, wherein the electrically activated component is configured to deliver therapeutic energy to tissue.

8. The surgical instrument of claim 1, wherein the dielectric cover comprises polytetrafluoroethylene.

9. The surgical instrument of claim 1, wherein the dielectric cover is heat shrunk over the second conductive plate.

10. The surgical instrument of claim 1, wherein the second conductive plate comprises a leaf spring configuration.

11. The surgical instrument of claim 1, further comprising a power source housed within the body, wherein the electrical contact assembly is configured to electrically couple the power source housed within the body with the electrically activated component of the cartridge assembly.

12. The surgical instrument of claim 1, wherein the channel assembly is configured to electrically ground the second conductive plate when the cartridge assembly is coupled with the channel assembly.

13. The surgical instrument of claim 1, wherein the shaft assembly comprises a circuit board.

14. The surgical instrument of claim 13, wherein the first conductive plate is in electrical communication with the circuit board.

15. The surgical instrument of claim 14, further comprising an electrical trace extending between the first conductive plate and the circuit board.

16. The surgical instrument of claim 1, where the end effector further comprises an anvil.

17. The surgical instrument of claim 16, wherein the anvil is configured to pivot relative to the channel assembly from an open position to a closed position.

18. The surgical instrument of claim 1, wherein the channel assembly comprises a side wall, wherein the first conductive plate is attached to the side wall.

19. A surgical instrument comprising:
(a) a body;
(b) a shaft assembly extending distally from the body;
(c) an end effector, wherein the end effector comprises:
 (i) a channel assembly, and
 (ii) a cartridge assembly configured to selectively couple with the channel assembly, wherein the cartridge assembly comprises an electrically activated component; and
(d) an electrical contact assembly configured to electrically couple a power source with the electrically activated component of the cartridge assembly, wherein the electrical contact assembly comprises a capacitor, wherein the capacitor comprises a first conductive plate, a second conductive plate, and a dielectric cover associated with either the first conductive plate or the second conductive plate, wherein the dielectric cover is positioned between the first conductive plate and the second conductive plate when the cartridge assembly is coupled with the channel assembly.

20. A surgical instrument comprising:
(a) a shaft assembly;
(b) an end effector extending distally from the shaft assembly, wherein the end effector comprises:
 (i) a channel assembly, and
 (ii) a cartridge assembly configured to selectively couple with the channel assembly, wherein the cartridge assembly comprises an electrically activated component; and
(c) an electrical contact assembly configured to electrically couple a power source with the electrically activated component of the cartridge assembly, wherein the electrical contact assembly comprises a capacitor, wherein the capacitor comprises a first conductive plate, a second conductive plate, and a dielectric cover associated with either the first conductive plate or the second conductive plate, wherein the dielectric cover is positioned between the first conductive plate and the second conductive plate when the cartridge assembly is coupled with the channel assembly.

* * * * *